(12) United States Patent
Song et al.

(10) Patent No.: US 7,378,067 B2
(45) Date of Patent: May 27, 2008

(54) APPARATUS FOR RETAINING AND HEAT SANITIZING ARTICLES

(75) Inventors: James Song, Henderson, NV (US); H. Bart Berens, Henderson, NV (US)

(73) Assignee: Germ Terminator Corporation, Henderson, NV (US)

( * ) Notice: Subject to any disclaimer, the term of this patent is extended or adjusted under 35 U.S.C. 154(b) by 627 days.

(21) Appl. No.: 10/468,596

(22) PCT Filed: Feb. 26, 2002

(86) PCT No.: PCT/US02/05526

§ 371 (c)(1),
(2), (4) Date: Jan. 27, 2004

(87) PCT Pub. No.: WO02/068003

PCT Pub. Date: Sep. 6, 2002

(65) Prior Publication Data

US 2004/0126274 A1    Jul. 1, 2004

Related U.S. Application Data

(60) Provisional application No. 60/270,907, filed on Feb. 26, 2001.

(51) Int. Cl.
*A61L 2/07* (2006.01)
(52) U.S. Cl. .................... 422/298; 422/299; 422/307; 392/405; 392/406
(58) Field of Classification Search .............. None
See application file for complete search history.

(56) References Cited

U.S. PATENT DOCUMENTS

| 726,926 | A | | 5/1903 | Hoffman |
| 2,340,206 | A | | 1/1944 | Richards |
| 3,267,678 | A | * | 8/1966 | Camp ......................... 60/670 |
| 3,950,867 | A | * | 4/1976 | Mazzolla ....................... 38/66 |
| 4,517,159 | A | * | 5/1985 | Karlson ....................... 422/20 |
| 4,544,529 | A | | 10/1985 | Hoeck |
| 4,582,076 | A | | 4/1986 | Prat |
| 4,835,363 | A | * | 5/1989 | Hoffmann ................... 219/258 |
| 5,019,344 | A | | 5/1991 | Kutner et al. |
| 5,277,875 | A | | 1/1994 | Albright et al. |
| 5,431,879 | A | | 7/1995 | Heyl et al. |
| 5,552,113 | A | | 9/1996 | Jennings |
| 5,637,280 | A | | 6/1997 | Nevell et al. |

(Continued)

FOREIGN PATENT DOCUMENTS

DE    3 332 172    3/1985

(Continued)

*Primary Examiner*—E. Leigh McKane
(74) *Attorney, Agent, or Firm*—Fitzpatrick, Cella, Harper & Scinto

(57) ABSTRACT

An article 100 and realted methods for reducing a microbial population on an article 168, wherein apparatus 100 includes a chamber in an article-holding basket 164 retains article 168 in an up-right position within the cahbmer an enclosing article 168. A heating system 172 introduces dry heat, moist heat, and, if desired, a combination of moist heat and dry heat into the chamber. A fluid supply system delivers a predetermine amount of fluid to a heating reservoir 174, which is disposed above heating system 172 to provide the moist heat.

43 Claims, 15 Drawing Sheets

U.S. PATENT DOCUMENTS

| | | | |
|---|---|---|---|
| 5,896,864 A * | 4/1999 | Boyle et al. | 132/228 |
| 5,919,416 A | 7/1999 | Auner | |
| D413,986 S | 9/1999 | Lin | |
| 6,039,926 A | 3/2000 | Goldman | |
| 6,565,819 B1 | 5/2003 | Herrera | 422/298 |

FOREIGN PATENT DOCUMENTS

| | | |
|---|---|---|
| EP | 0 183 956 | 6/1986 |
| GB | 2 336 313 | 10/1999 |

* cited by examiner

APPARATUS FOR RETAINING AND HEAT SANITIZING ARTICLES

This application claims benefit of U.S. Provisional Patent Application No. 60/270,907 filed Feb. 26, 2001.

FIELD OF THE INVENTION

The present invention generally relates to an apparatus, including a fluid-supply system, a heating system, and an article-holding basket, for securing, enclosing, and reducing, if not eliminating, the microbial population present on the surfaces of one or more articles contained in the apparatus. The invention also is directed to related methods. Hereinafter for economy of expression, the process of reducing, if not eliminating, the microbial population present on the surfaces of articles is generally referred to as reducing a "microbial population" or reducing "microbial populations" present on the surfaces of articles, which expressions are interchangeably used herein. More particularly, the present invention relates to an apparatus and method for reducing the microbial population present on the surfaces of articles, including personal hygiene instruments, implements, and dental handpieces, such as oral hygiene instruments (e.g., toothbrushes, tongue scrapers, and the like). Hereinafter, again for economy of expression, personal hygiene instruments, such as oral hygiene instruments, implements, and dental handpieces are generally referred to as "articles." Even more particularly, the present invention relates, in one embodiment, to an apparatus and method for reducing the microbial population present on the surfaces of articles, by subjecting such articles, in order, to moist heat and then to dry heat, which synergistically provide efficacious results in reducing the microbial population present on the surfaces of the articles. In another embodiment, the present invention relates to an apparatus and method for reducing the microbial population present on the surfaces of the articles by subjecting the articles only to moist heat. The present invention also features a heating system and an article-holding basket for use in such an apparatus.

BACKGROUND

It is known that personal hygiene articles, including oral hygiene instruments, such as toothbrushes, tongue scrapers, and the like, may have substantial microbial populations present on their surfaces. It is also known that such microbial populations can contribute to the spread of diseases, such as gum disease, tooth decay, bad breath, mouth sores, and other chronic illnesses and infectious diseases. Indeed, medical studies indicate that many illnesses, such as heart disease, and bacterial infections can be traced to microorganisms (e.g., germs, bacteria, viruses, pathogenic microorganisms, yeast, fungi, and the like) present on the surfaces of such personal hygiene articles, which microorganisms are transferred to soft human tissue, such as the gums or tongue or that otherwise may enter the bloodstream during use of the articles. Scientific research confirms that a wide spectrum of bacterial and viral agents can survive for substantial periods of time on unprotected toothbrushes. Such bacterial and viral agents include microbes such as influenza, Herpes Simplex virus, salmonella, *E-coli*, listeria, staphylococci, candida, gingivitis, gum disease causing bacteria, and viruses that can cause the common cold are debilitating, even potentially deadly, diseases. It is estimated that 75 percent of Americans suffer from some form of gum disease and 90 percent of all systemic diseases including kidney disease, diabetes, and heart disease have oral manifestations. Again, for economy of expression, such bacterial and viral agents, and microorganisms of all types are generally referred to as a "microbial population" or "Microbial populations", which expressions are interchangeably used herein.

Accordingly, it is also known that reducing the microbial population present on the surfaces of articles can reduce the spread of illnesses and infectious diseases transferred by use of such articles.

The present inventors recognized that reducing the microbial population present on the surfaces of personal hygiene articles, and maintaining such articles in their reduced-microbial population state between uses pose two, related challenges. First, during normal use, personal hygiene articles may routinely collect contaminants, such as, particles of food, germs, bacteria, viruses, and the like, which may be present in the user's mouth. Many of these contaminants are normally removed from the articles by rinsing such after use. However, it is highly probable that not all contaminants will be removed by rinsing the articles. Thus, at least some of these contaminants often remain on the articles after use and provide a fertile breeding habitat for microbial populations. Second, personal hygiene articles, even if no microbial population is present on the surfaces of the articles after use, typically are not stored in a contaminant-free environment between uses. Instead, these articles are often stored in drawers or on vanity countertops, such as cups, trays, holders, and the like, which may have an evolving microbial population on their surfaces, all of which subject even microbial population-free articles to contamination after use. Moreover, the residual moisture on the articles after use fosters the growth of microbial populations on the surfaces of the articles. In addition, the articles are subject to contamination from the surrounding environment, including the ambient air, which in a typical household bathroom is commonly replete with microbial populations.

Several conventional approaches for reducing the microbial population present on the surfaces of personal hygiene articles, and the like, are known. However, all known conventional apparatuses and methods have one or more disadvantages.

One conventional approach is to soak the articles in a chemical disinfectant. Unfortunately, chemical disinfectants often have difficulty reaching all of the surfaces of some articles such as the surfaces between tightly compacted bristles found in many toothbrushes, especially if the exposure of the articles to the chemical disinfectant is brief. Accordingly, use of chemical disinfectants is not entirely effective. In addition, such chemical disinfectants are relatively costly and must be frequently resupplied. Further, repeated use of chemical disinfectants over time may present health concerns in their own right, such as inflammation of soft human tissue and damage to the enamel of teeth.

Another conventional approach is to reduce the microbial population present on personal hygiene articles using microwave energy. So-called microwave disinfecting is problematic because of the electrical arcing that occurs at any metal components used in the articles, such as the metal cleats sometimes used to anchor the bristles in a toothbrush head. Microwaving also tends to deform the thermoplastic materials of which many personal hygiene articles are made, at least in part, resulting in articles that are unusable. Additionally, most households are not equipped with microwave apparatuses outside of the kitchen. Accordingly, use of this approach tends to be inconvenient for many household users.

Still another conventional approach to reduce the microbial population present on the surfaces of personal hygiene articles is to expose the articles to ultraviolet light. However, effective, ultraviolet light equipment tends to be expensive and tends to require regular maintenance by a skilled technician. Also, ultraviolet light cannot always reach all surfaces of the articles, such as between the tightly compacted bristles found in many toothbrushes. Further, ultraviolet light degrades some thermoplastic materials. Moreover, repeated exposure of a user to ultraviolet light may present safety concerns, such as, accidental vision damage.

Yet another conventional approach is to subject personal hygiene articles to a steam and pressure treatment in an apparatus, such as an autoclave. However, generating the steam and pressure requires special equipment, such as a heat source or a microwave source and a compressor and requires an inconvenient amount of time to start and complete the process. Moreover, such an apparatus tends to be bulky and expensive to buy and to maintain. Also, such an apparatus generally yields moist articles that are ripe for the growth of evolving microbial populations. Further, such an apparatus poses certain burn risks, such as scalding, because of the use of pressurized steam. Therefore, such an apparatus generally does not appeal to household users.

There are many types of methods and apparatus that attempt to overcome the aforesaid problems. For example, U.S. Pat. No. 5,919,416 (Auner) is directed to a sterilization process for thermoplastic appliances. In the apparatus of Auner, water contained in a reservoir of an uncovered sterilization tray is brought to, or near to, its boiling point by an initial exposure cycle to microwave energy. Thereafter, the appliance, i.e., a toothbrush, is placed in a sterilization tray in proximity to the microwave-preheated water. The sterilization tray is then covered and subjected to an additional (shorter) exposure cycle of microwave energy. The water in the reservoir boils, and steam fills the covered container and pressurizes it to about 10 psi. The steam and the microwave energy sterilize the toothbrush. However, Auner neither dries the sterilized toothbrush nor provides a satisfactory sanitary storage environment after a sterilization operation is performed. Further, the pressurized moist heat may present the above-noted burn risks.

U.S. Pat. No. 5,019,344 (Kutner, et al.) relates to a method for sterilizing articles, such as dental handpieces. Kutner, et al. discloses introducing the articles and a liquid sterilant solution into a collapsible pouch, sealing the pouch, and heating the sealed pouch to vaporize the liquid sterilant solution to produce an atmosphere of hot, sterilant vapor. The articles are sterilized under the combined effects of the chemical vapor and microwave irradiation. However, this method does not prevent deforming the thermoplastic material of the articles. Further, a user must open the pouch and handle the wet, sterilized articles, thereby subjecting the articles to contamination.

G.B. Patent Document No. 2,336,313 A (Lin) is directed to a toothbrush sterilizer consisting of a container for sterilizing the bristles of a toothbrush comprising a water vessel and a water heater to generate steam to sterilize the bristles of the toothbrushes held by racks, which are located inside a cylindrical body. Ventilation holes may be provided in the top of the cylindrical body. The water vessel is provided with a recess for holding water. Located over the water vessel is a perforated disc-like cover, having a plurality of pores. Located under the water vessel is a water heater. When a switch is turned on, the water contained in the water vessel is heated by the water heater to produce steam, which passes through the pores of the disc-like cover to sterilize the bristles of the toothbrush. The handles and heads of the toothbrushes are also sterilized. The Lin apparatus may be subject to the safety concerns relating to the use of a significant amount of steam to sterilize toothbrushes. Moreover, the Lin apparatus requires a certain amount of start-up time after switching on the toothbrush sterilizer, which is an inconvenience to the user.

U.S. Design Pat. No. 413,986 (Lin) discloses a container for sterilizing toothbrushes using steam.

As above-noted, conventional apparatuses and methods have one or more disadvantages, which make their use unappealing and/or disadvantageous to most household users. Accordingly, there is a need for a compact, inexpensive, safe, easy- and ready-to-use, and effective household apparatus that reduces the microbial population present on the surfaces of articles, including personal hygiene articles, such as toothbrushes, after each use by subjecting the articles to moist heat and, in particular, in turn to moist heat and then to dry heat.

Accordingly, there is a need for an apparatus that stores articles, after reducing the microbial population present on the surfaces of such articles, in a reduced microbial environment between uses without requiring user handling of the articles until their next use.

Even further, there is a need for a fluid-supply system for use in such an apparatus.

Yet further, there is a need for a safe and convenient heating system for use in such an apparatus.

In addition, there is a need for an article-holding basket adapted and configured for use in such an apparatus.

SUMMARY OF THE INVENTION

It is a general object of the present invention to provide an apparatus, including a fluid-supply system, a heating system, an article-holding basket, and a method for reducing the microbial population present on the surfaces of articles, including personal hygiene articles, such as toothbrushes.

It is one object of the present invention to provide an apparatus, including a fluid-supply system, a heating system, an article-holding basket, and a method for reducing the microbial population present on the surfaces of articles, including personal hygiene articles, such as toothbrushes, without the need for solvents, radiation, ozone, ionization, chlorine, alcohol, bleach, or other chemicals.

It is another object of the present invention to provide an apparatus, including a fluid-heating supply system, a heating system, an article-holding basket, and a method for reducing the microbial population present on the surfaces of articles, including personal hygiene articles, such as toothbrushes, that is safe and easy to use and provides quick and effective results.

It is a further object of the present invention to provide a method for reducing the microbial population present on the surfaces of articles by exposing the articles at least to moist heat.

It is yet a further object of the present invention to provide a method for reducing the microbial population present on the surfaces of articles by exposing the articles at least to dry heat.

It is yet another object of the present invention to provide a sanitary environment for storing articles, including personal hygiene articles, such as toothbrushes, after reducing the microbial population present on the surfaces of the articles, and to provide such an environment wherein there is no need to handle the articles after such have been subjected to a microbial-population reducing operation until their next use.

Accordingly, the invention in one aspect is directed to a compact, inexpensive, energy-efficient apparatus for reducing the microbial population present on the surfaces of articles, including personal hygiene articles, such as toothbrushes, and for storing the articles after the microbial-population reducing operation until their next use.

These and other aspects, objects, and features of the present invention will become apparent from the following detailed description of the preferred embodiments, read in conjunction with, and reference to, the accompanying drawings.

BRIEF DESCRIPTION OF THE DRAWINGS

FIG. 1b is an exploded, perspective view of the apparatus shown in FIG. 1a.

FIG. 7b is a top, plan view of the heating system shown in FIG. 7a.

FIG. 8b is a top, plan view of the article-holding basket shown in FIG. 8a.

DETAILED DESCRIPTION OF A PREFERRED EMBODIMENT

Initially, for convenience of explanation herein, the attitude, orientation, and location of the components of the apparatus of the present invention will be defined with reference to a fully-assembled apparatus as viewed in normal use. Therefore, the word "horizontal," refers to an orientation parallel with a surface on which the apparatus is supported in normal use. Similarly, the word "vertical" refers to an orientation substantially perpendicular to the horizontal orientation. Further, the word "bottom" refers to the bottom of the apparatus closest to the surface on which the apparatus is supported, while the word "top" refers to the end of the apparatus, which is opposite to the bottom. The words "front", "rear", "left side" and "right side" of the apparatus are relative terms for depicting the apparatus as it appears in the appended drawings.

In the discussion which follows, as well as in the appended drawings, a toothbrush has been described and depicted, respectively, as an exemplary article, the microbial population present on the surfaces of which may be reduced by use of the present invention. Nonetheless, articles having components different from that described and depicted, including other articles, which are entirely different from that described and depicted, such as, dental handpieces, other personal hygiene articles, and the like, may also benefit from use of the present invention. Thus, while reference has been, and will hereinafter be made to a "toothbrush" or "toothbrushes," as an exemplary article, it will be understood that any such reference is intended to conveniently refer to one form of an article, the microbial population present on the surfaces of which may be reduced by use of the present invention, but not to limit the present invention thereto. Although one article is shown in the apparatus, it will be understood that the apparatus can be adapted and configured to accommodate more than one article, and the present invention is not limited to an apparatus and method for accommodating only one article.

Figure 1A:
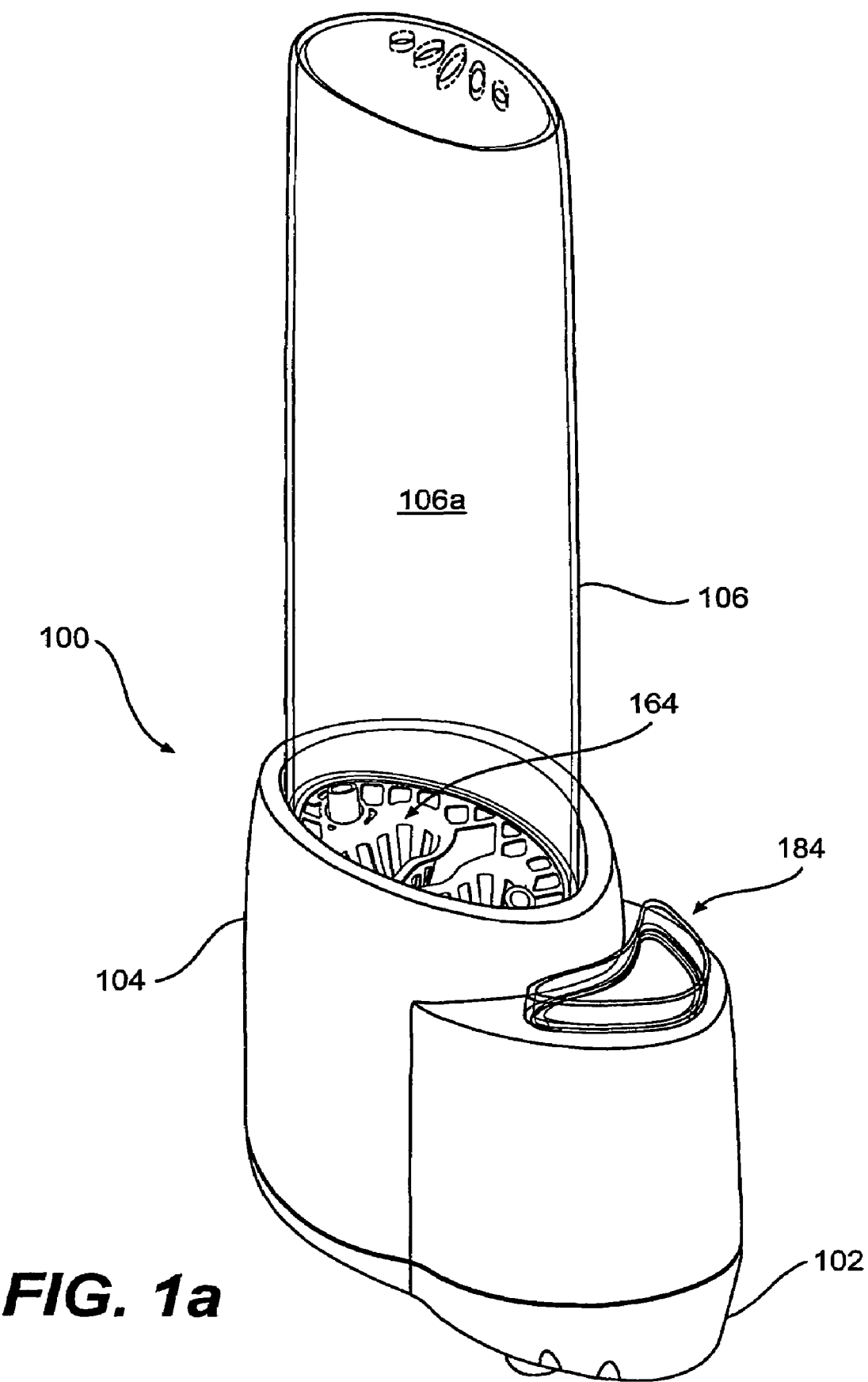
FIG. 1a is a perspective view of the apparatus according to a preferred embodiment of the invention.
Figure 1B:
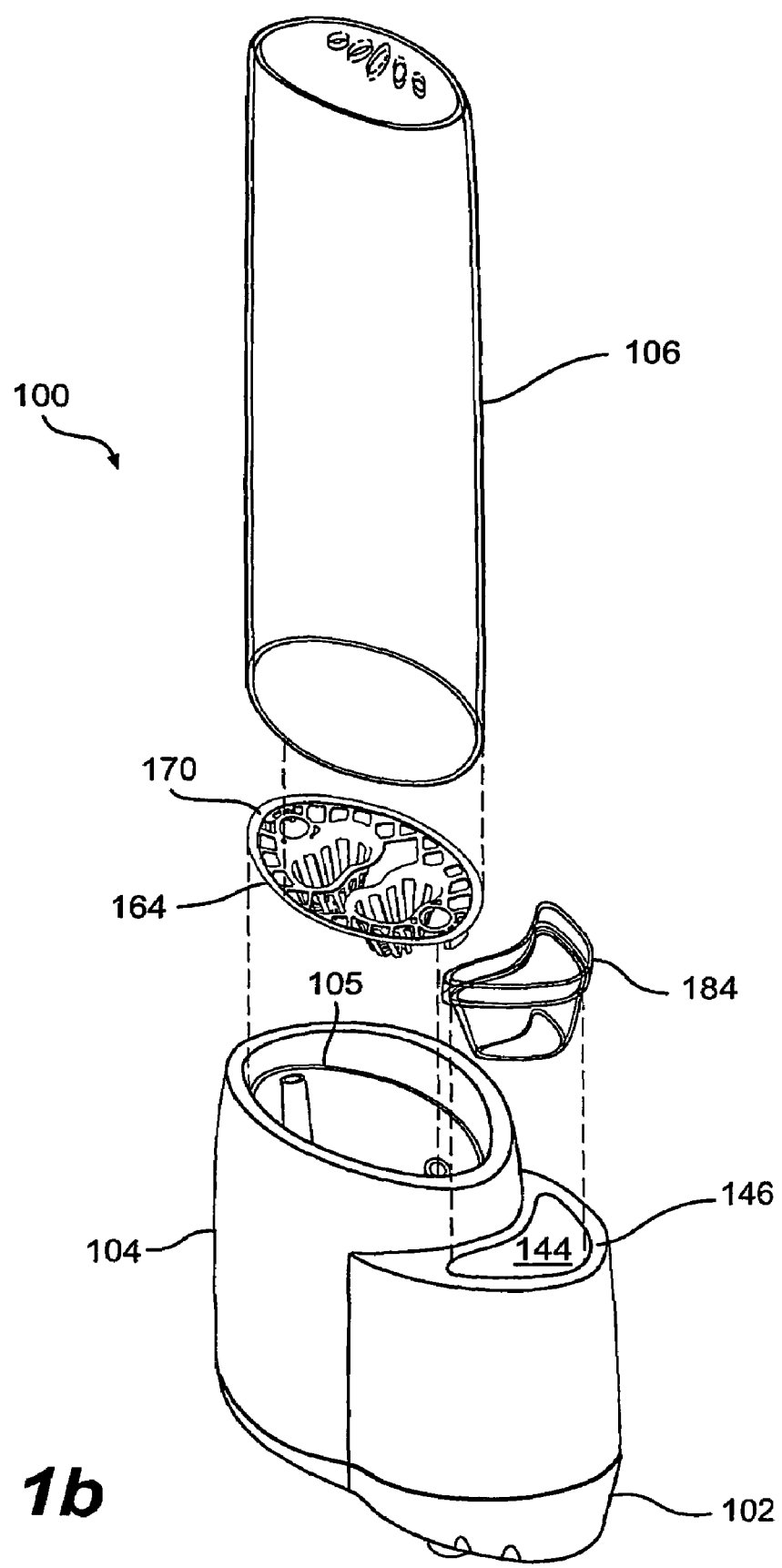
Figure 1C:
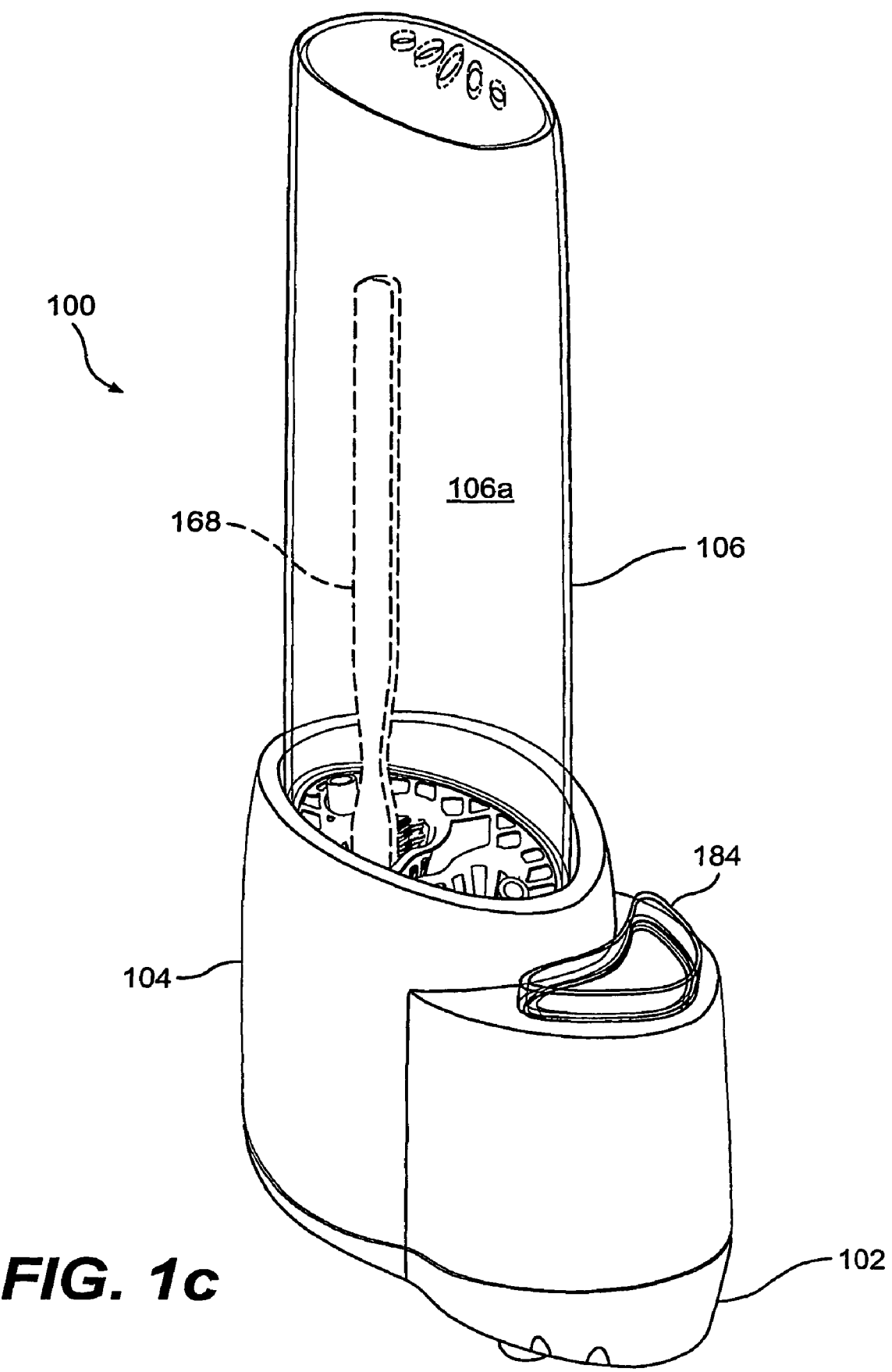
FIG. 1c is a perspective view of the apparatus shown in FIG. 1a with a conventional toothbrush secured and enclosed therein.

In FIGS. 1a, 1b, and 1c, the apparatus 100, according to a preferred embodiment of the present invention, is shown to be generally vertically-oriented and includes a body 104 seated on and removably secured to base 102. A removable cover 106 extends vertically upwardly from the body 104 and its interior space defines an upper chamber 106a for enclosing a top portion of an article 168, shown as a toothbrush, the surface microbial population of which is to be reduced. In addition, a measuring cup 184 is stored in a cavity 144 formed in the body 104 of the apparatus. An article-holding basket 164 is removably disposed inside the body 104.

As illustrated, the basket 164 and the cover 106 share the same cross-sectional shape and dimensions where they meet so that the article-holding basket 164 snugly fits into a lower chamber 104a formed in body 104 while being supported on a shoulder 105 formed on an inner surface of lower chamber 104a. The open end 106a of the cover rests on the peripheral flange 170 of the article-holding basket 164. Upper chamber 106a and lower chamber 104a will be collectively referred to herein simply as either a chamber or chamber 104a, 106a.

Figure 2:
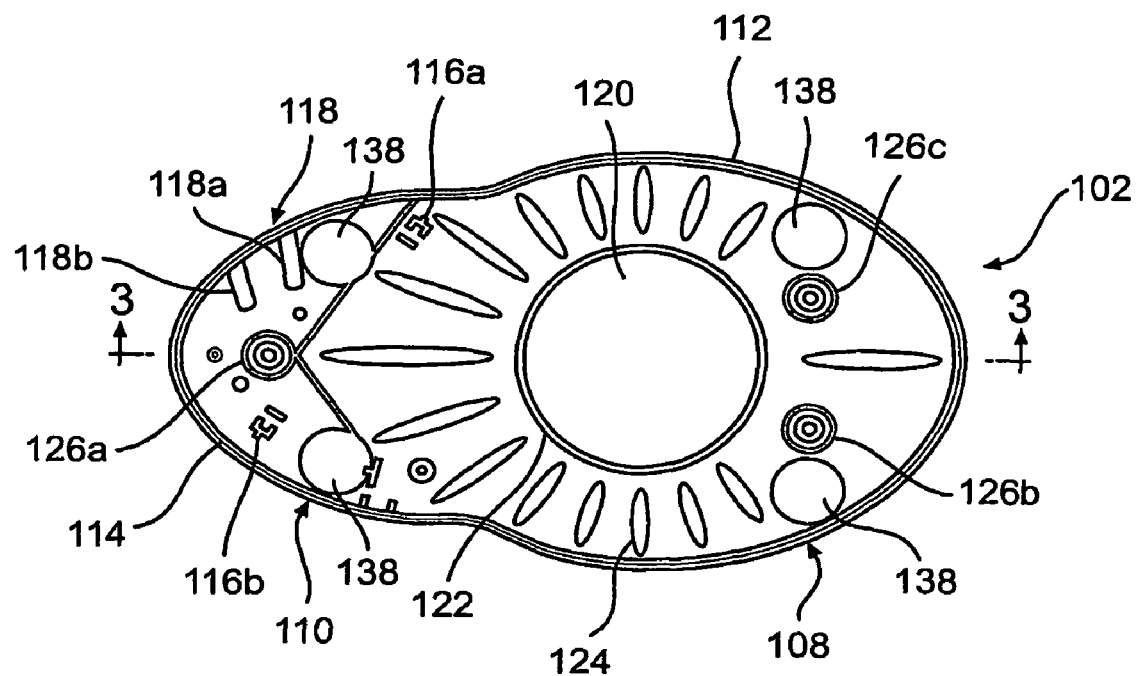
FIG. 2 is a top, plan view of a base of the apparatus shown in FIGS. 1a, 1b, and 1c.
Figure 3:
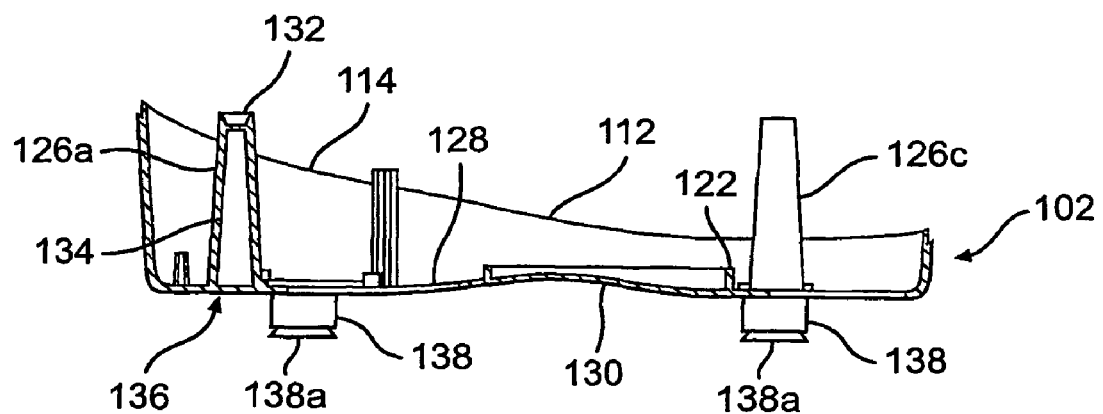
FIG. 3 is a cross-sectional view of the base taken along line 3-3 in FIG. 2.

FIGS. 2 and 3 show the base 102, which is generally shaped like two integrally-formed, partially-overlapping ellipses with a larger elliptical region 108 toward the right side of the figure and a smaller elliptical region 110 located toward the left side of the figure. However, it is to be understood that the shape and dimensions of the base 102, body 104, and cover 106 may vary depending on, inter alia, the shape, dimensions, and number of articles to be processed, in the apparatus 100, as well as various other design and aesthetic considerations.

The base 102 generally includes a bottom wall 128 and a contoured peripheral wall 112 extending upwardly from the perimeter of the bottom wall. The perimeter sidewall 112 preferably is integrally molded therewith. Thus, the shape of the sidewall 112 corresponds to the perimeter of the body 104. A shoulder 114 is formed at a top of sidewall 112. The bottom wall 128 has an upward contoured portion 130 formed near the substantial center of the base 102. The contoured portion 130 provides additional strength to the bottom wall 128. The contoured portion 130 also increases the space between the lower surface of the bottom wall 128 and the surface on which the apparatus is supported thereby improving airflow around and into the apparatus 100.

A heat reflector 120, which may be circular, is disposed on an upper surface of and is located near a substantial center of the bottom wall 128. The heat reflector 120 is located under a heating element to be described hereafter and is in close proximity thereto, so as to reflect radiant heat emitted from a heating element. This arrangement is particularly advantageous, inasmuch as it maximizes the amount of heat reflected upwardly toward a heating reservoir (not shown), which is disposed in the body 104. The heat reflector 120 is typically made from an efficient, heat-reflective material, such as aluminum foil, which may be adhered to a surface of the bottom wall 128. However, it will be understood that other materials also may be suitable for this purpose. The heat reflector 120 is surrounded by a low circumferential wall 122. A plurality of elliptical vents 124 are formed in the base 102 and extend radially outwardly from the heat reflector 120. The vents 124 allow ambient air to flow into the apparatus from below to the apparatus.

The base 102 also includes three structural members 126a, 126b, and 126c, which provide support for the body 104. According to a preferred embodiment, one structural member 126a is located at the left side of the heat reflector 120 and two structural members 126b, 126c are located at the right side of the heat reflector 120. Each structural member 126a, 126b, and 126c is generally shaped as a vertically-tapered, truncated cone extending upwardly from the top surface of the bottom wall 128. Further, each structural member 126a, 126b, and 126c is preferably integrally formed with the base 102. The positioning and dimensions of the structural members 126a, 126b, and 126c may vary depending on, inter alia, the weight and dimensions of the body 104.

Figure 5:
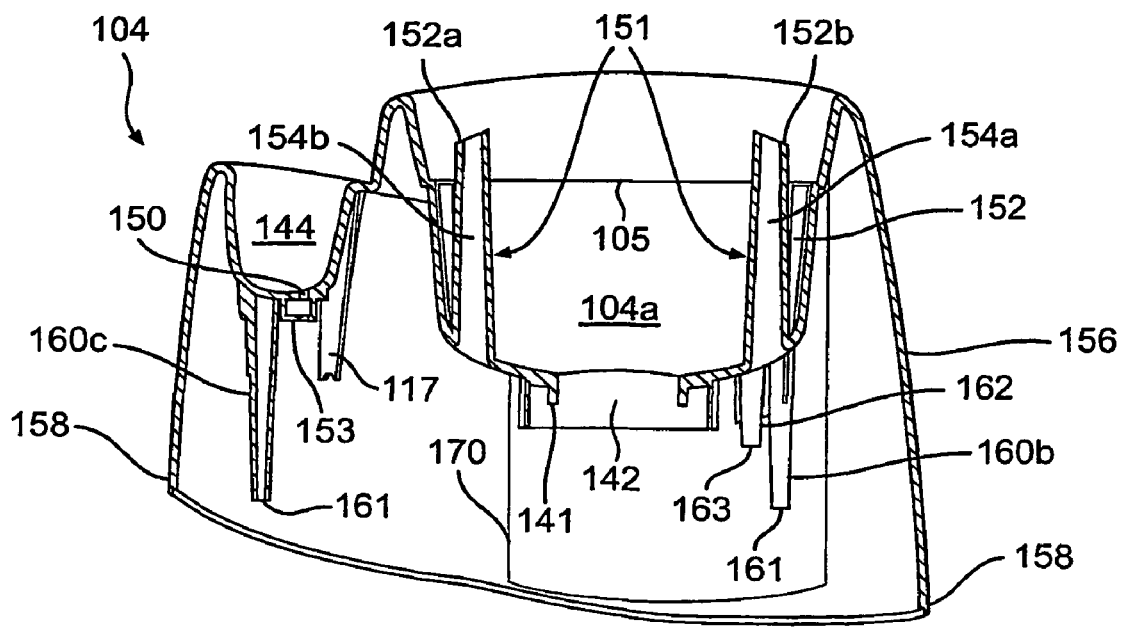
FIG. 5 is a cross-sectional view of the body taken along line 5-5 in FIG. 4.

The top of each of the structural members 126a, 126b, and 126c includes a recess 132 dimensioned to receive the lower ends of corresponding support posts provided in the body 104. (Two support posts 160b, 160c are shown in FIG. 5.) The structural members 126a, 126b, and 126c and their corresponding support posts may be joined by fasteners. Each structural member 126a, 126b, and 126c includes a throughhole 134 extending from an opening 136 in the bottom wall 128 of the base 102 through the recess 132. A tool may be inserted into the throughhole to secure the fasteners to join the structural members 126a, 126b, and 126c to their corresponding support posts 126a, 126b, and 126c formed in body 104.

The base 102 further includes a circuit board holder to secure a circuit board (not shown) from horizontal movement. The circuit board holder includes a first side holder 116a and a second side holder 116b. Each side holder has a "channeled-shaped" crosssection. The side holders 116a, 116b are dimensioned and disposed so that their respective open ends oppose and securely receive opposing edges of the circuit board, which may be positioned by simply sliding it between the first side holder 116a and the second side holder 116b. The holders 116a, 116b extend vertically upward from the base and are preferably integrally molded therewith.

Figure 11:
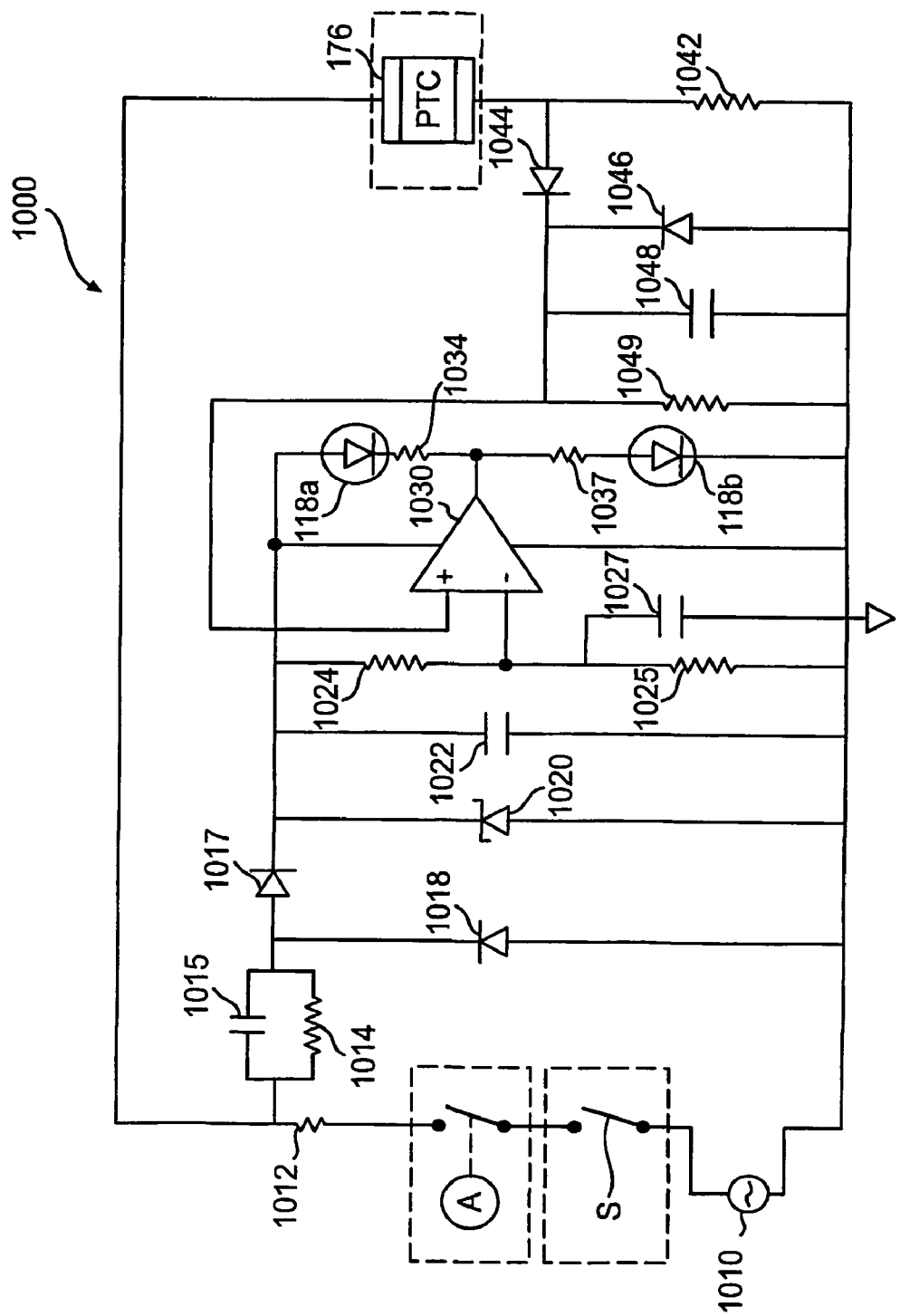
FIG. 11 is a schematic diagram of a power supply and current sensing circuit in accordance with a preferred embodiment of the invention.

A power supply and current sensing circuit 1000, which will be discussed later in connection with FIG. 11, is printed or otherwise formed on the circuit board.

A status indicator 118, which is responsive to the power supply and current sensing circuit 1000, is provided on the base 102 and includes two different-colored, light emitting diodes (LEDs) 118a, 118b, so as to be externally visible. One LED 118a, red-in-color in one embodiment of the invention, indicates to the user that a moist-heat generating mode is in operation. The other LED 118b, green-in-color in one embodiment of the invention, indicates that a dry-heat generating mode is in operation.

Four support feet 138 are provided on the bottom surface of the bottom wall 128. The support feet 138 not only provide support for the apparatus 160 but also allow additional space between the apparatus 100 and the surface on which it is supported, thereby allowing increased airflow around and into the bottom of the apparatus. The support feet 138 are preferably integrally molded to the underside of the bottom wall 128.

Each support foot 138 may include at its distal end 138a a "nonslip" surface, which may include a pad made of, for example, rubber or the like, to increase the friction between the feet and the surface on which the apparatus 100 is supported. This arrangement is advantageous, inasmuch as the apparatus is likely to be used on a smooth, wet surface in a high-humidity environment, such as on a damp vanity countertop in a bathroom.

Figure 4:
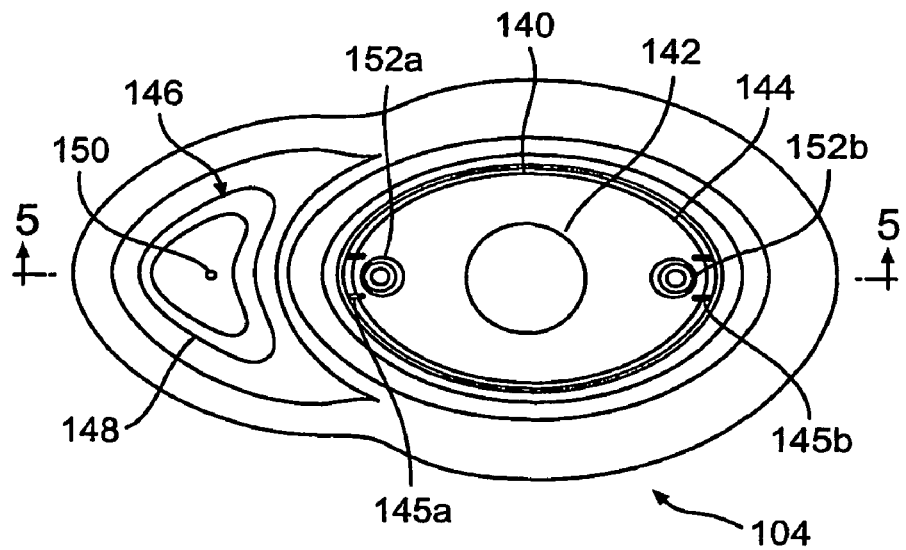
FIG. 4 is a top, plan view of a body of the apparatus shown in FIGS. 1a, 1b, and 1c.

In FIGS. 4 and 5, the body 104 of the apparatus generally includes a contoured outer wall partially defining the lower chamber 104a. The lower chamber 104a has a center, bottom opening 142, a circumferential shoulder 144, and a pair of guide channels 145a, 145b formed in an interior surface thereof and disposed at opposing ends of lower chamber 104a. The lower chamber 104a and bottom opening 142 are illustrated, for example, as being elliptical and circular, respectively.

The body 104 includes three body support posts 160a (not shown), 160b, and 160c arranged to seat on the structural members 126a, 126b, and 126c of the base 102, respectively. Consequently, two of the support posts 160a and 160b are located at the right side of the lower chamber 104a. The third body support member 160c is located at the right side of the lower chamber 140b. Of course, the exact position and dimensions of the body support members 160a, 160b, and 160c and structural members 126a, 126b, and 126c may vary.

Each of the body support members 160a, 160b, and 160c includes an internally-threaded hole 161 to accept a fastener, so as to join each body support member to its corresponding structural member 126a, 126b, and 126c thereby allowing the body 104 to be removably secured to the base 102.

A circumferential shoulder 105 is formed on an inside surface of the lower chamber 104a and is dimensioned to engage a flange 170 of a removable article-holding basket 164. The lower chamber 104a is shaped to receive the article-holding basket 164, which secures at least an end portion of at least one article. The lower chamber 104a is adapted and configured to direct downwardly flowing condensation toward a bottom opening 142.

The body 104 is adapted and configured to seat on the periphery of the base 102 and thus shares the same general cross-sectional dimensions as the base 102 where they meet. Sidewall 156 of body 104 has a groove 158 formed therein to seat against a shoulder 114 formed in the upper edge of sidewall 112 of the base 102.

A temperature-moderating system 151 is integrally formed inside the lower chamber 140b and includes a pair of ambient air delivery tubes 152a, 152b that extend vertically within the lower chamber 104a to allow ambient air into the lower chamber.

Each of the ambient air delivery tubes 152a, 152b has a throughhole 154a, 154b, respectively. The pair of ambient air delivery tubes 152a, 152b is located at the focii of the lower chamber 104a. Locating the ambient air delivery tubes 152a, 152b at the focii ensures that they will not interfere with the positioning and retention of the article-holding basket 164. However, the ambient air delivery tubes 152a, 152b may be located at other locations in the lower chamber 104a provided they do not interfere with positioning and retention of the article-holding basket 164.

When moist heat is produced, the ambient air delivery tubes 152a, 152b deliver ambient air to moderate the temperature of the moist heat within the chamber 104a, 106a. This ensures that the internal temperature of the apparatus does not rise to a level that will scald the user and will neither melt nor otherwise deform the article. Typically, the temperature at the inside center of the upper chamber 106a is between about 170° F. and about 180° F.

During an operation in which dry heat is generated, the ambient air delivery tubes 152a, 152b provide relatively dry ambient air to the chamber 140a, 140b, which is further dried and heated by the heater element so as to urge the moist heat air and vent upwardly by convection out of the apparatus 100 through the vent holes 188 formed in cover 106.

Two heating-element mounting posts 162, only one of which is seen in FIG. 5, extend downwardly from the exterior surface of the lower chamber 104a which, in fact, is inside body 104. The heating element mounting-posts provide structures to which a heating system mounts. Each mounting post includes an internally-threaded bore hole 163 to accept a fastener. The mounting posts 162 are located at opposing sides of the lower chamber 104a.

The body 104 also includes a fluid-supply reservoir 144 formed integrally therein and has a drain hole 150 provided at a bottom, center thereof (see FIG. 4). A collar 107 is integrally formed around drain hole 150 to receive a fluid-supply conduit.

A pair of concentric, annular projections 141, 142 is integrally formed in the bottom of lower chamber 104a. The projections provide a gasket receiving portion.

Another circuit board holder 117 formed in body 104 secures the top edge of the circuit board from vertical movement when the base 102 and the body 104 are assembled.

Figure 6:
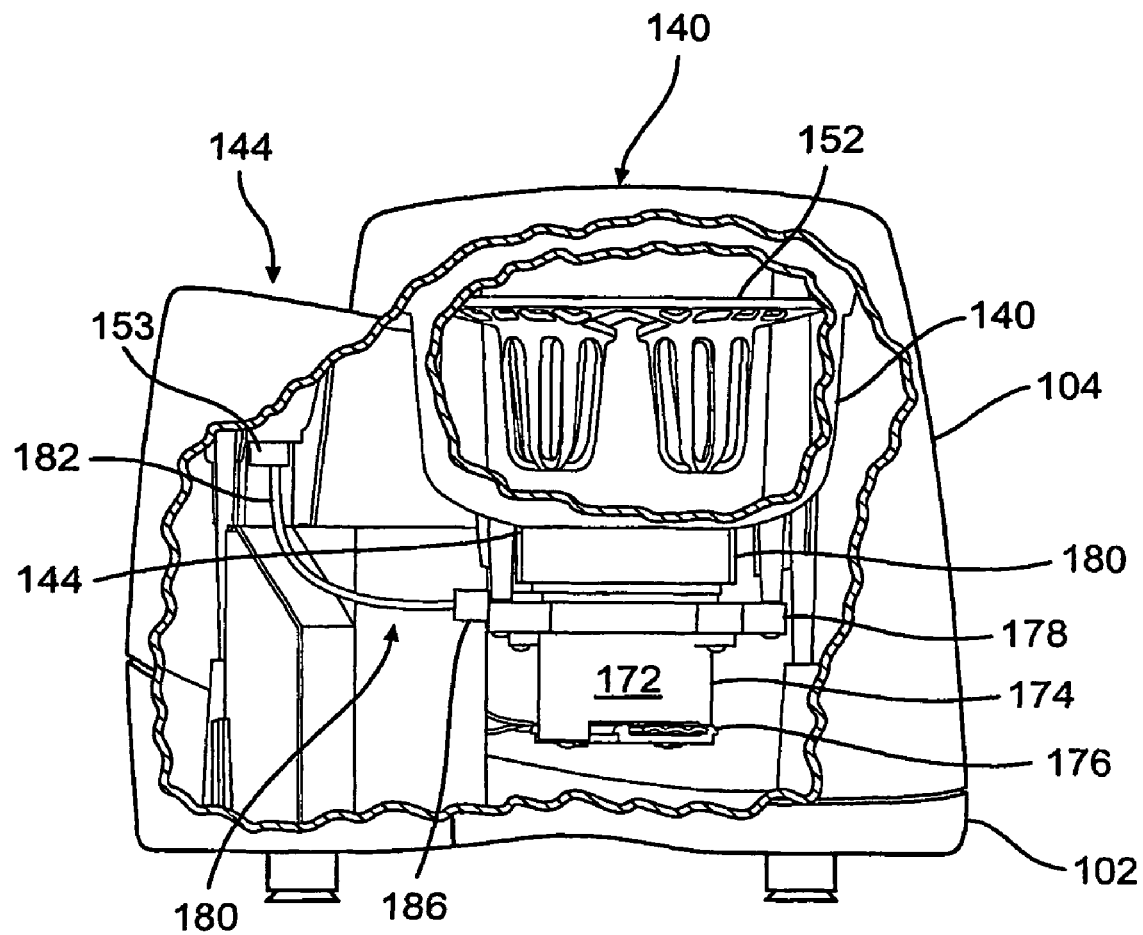
FIG. 6 is a partially-fragmented, front, elevational view of the base and body, with a portion of the outer walls of the base and body, as well as a portion of the wall of a lower chamber inside the body removed.
Figure 7A:
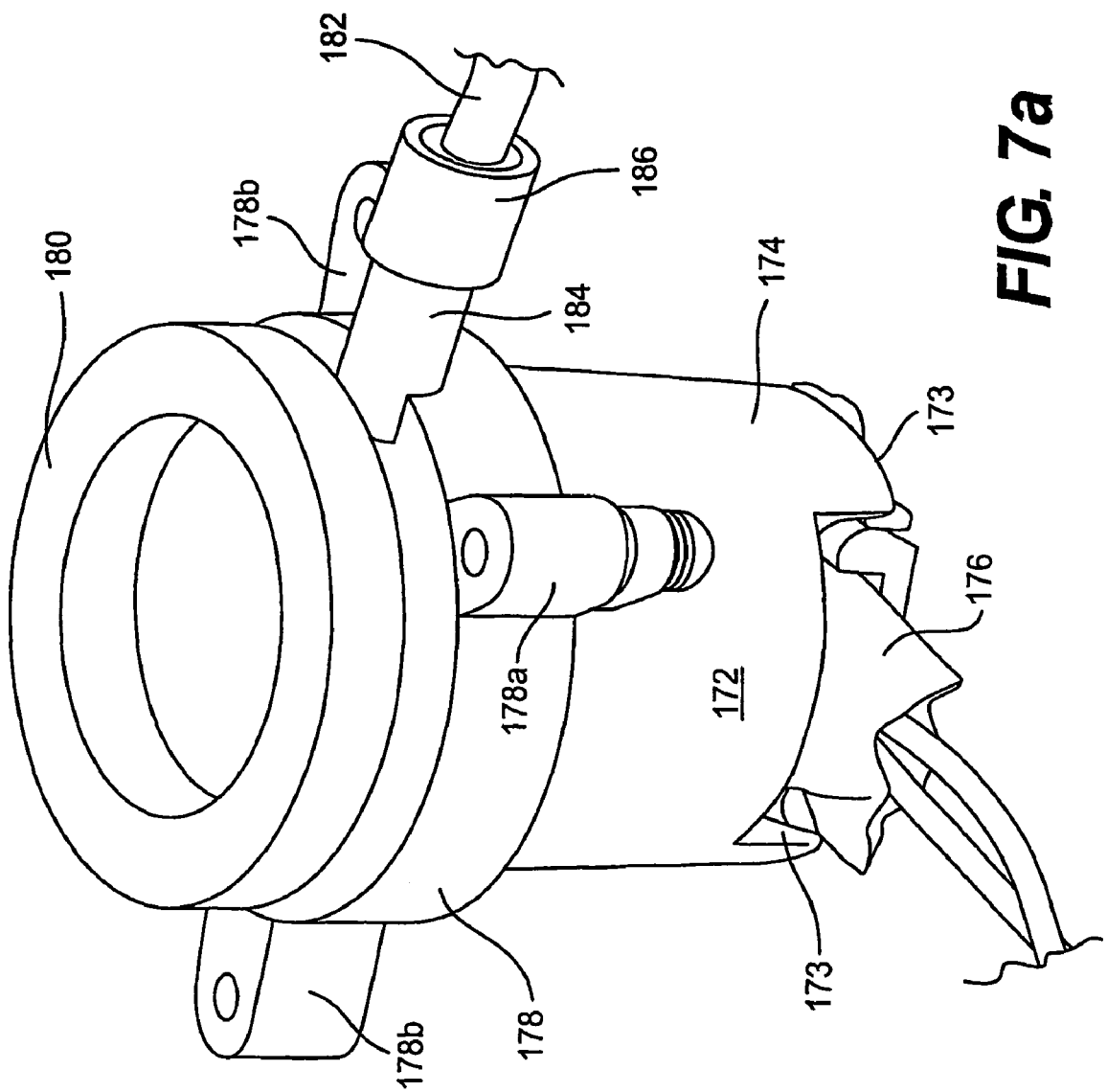
FIG. 7a is a perspective view of a heating system according to a preferred embodiment of the invention.
Figure 7B:
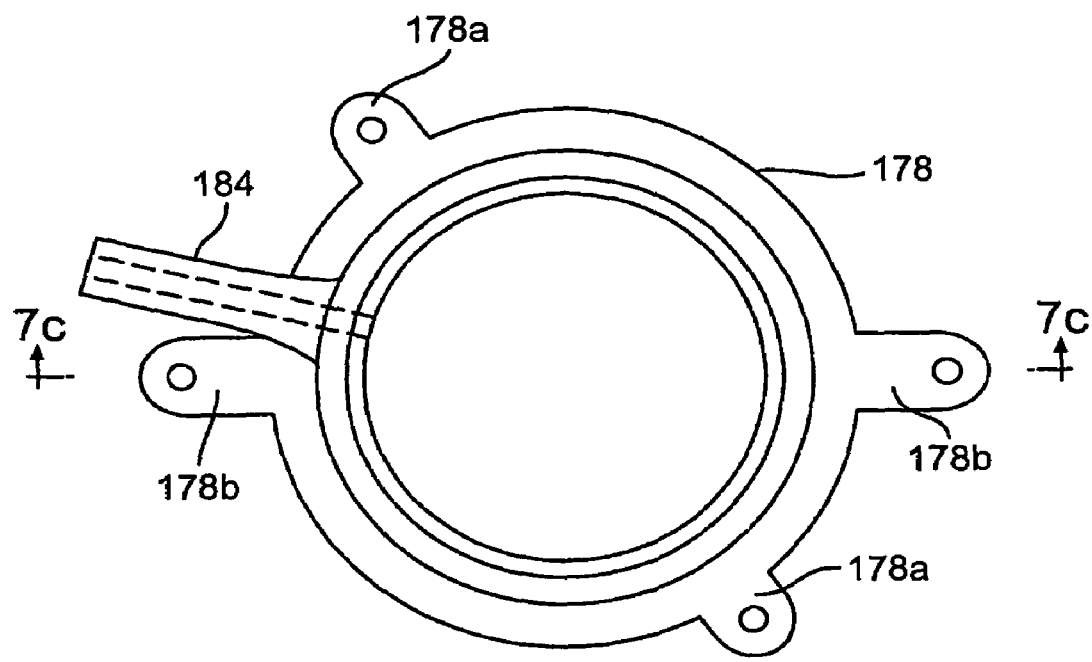
Figure 7C:
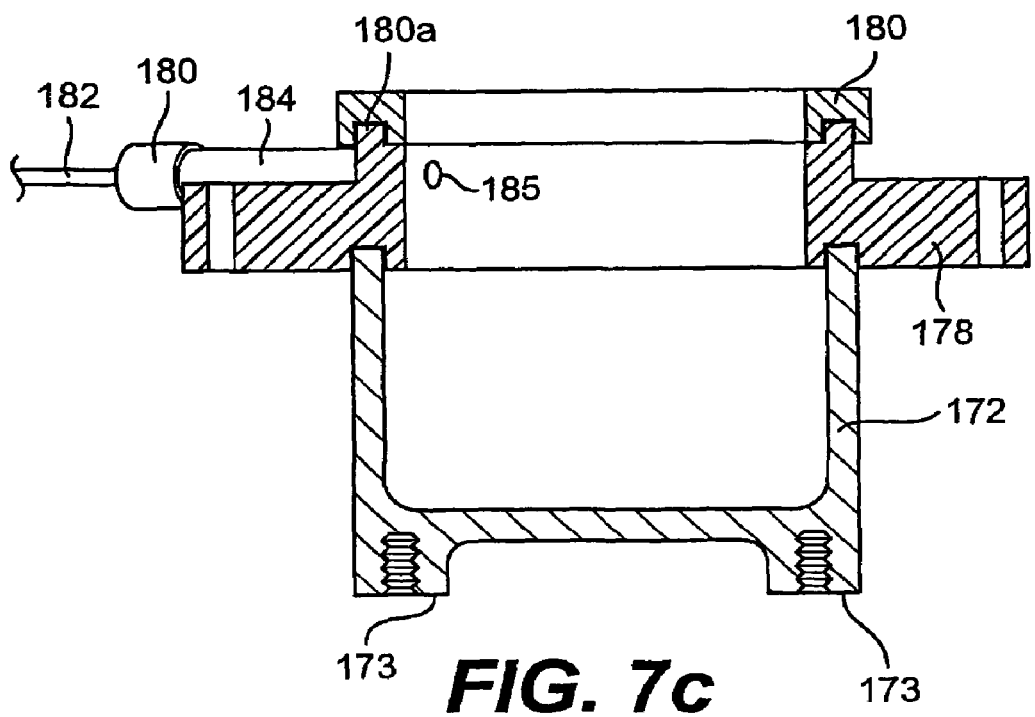
FIG. 7c is a cross-sectional view taken along line 7c-7c in FIG. 7b.
Figure 7D:
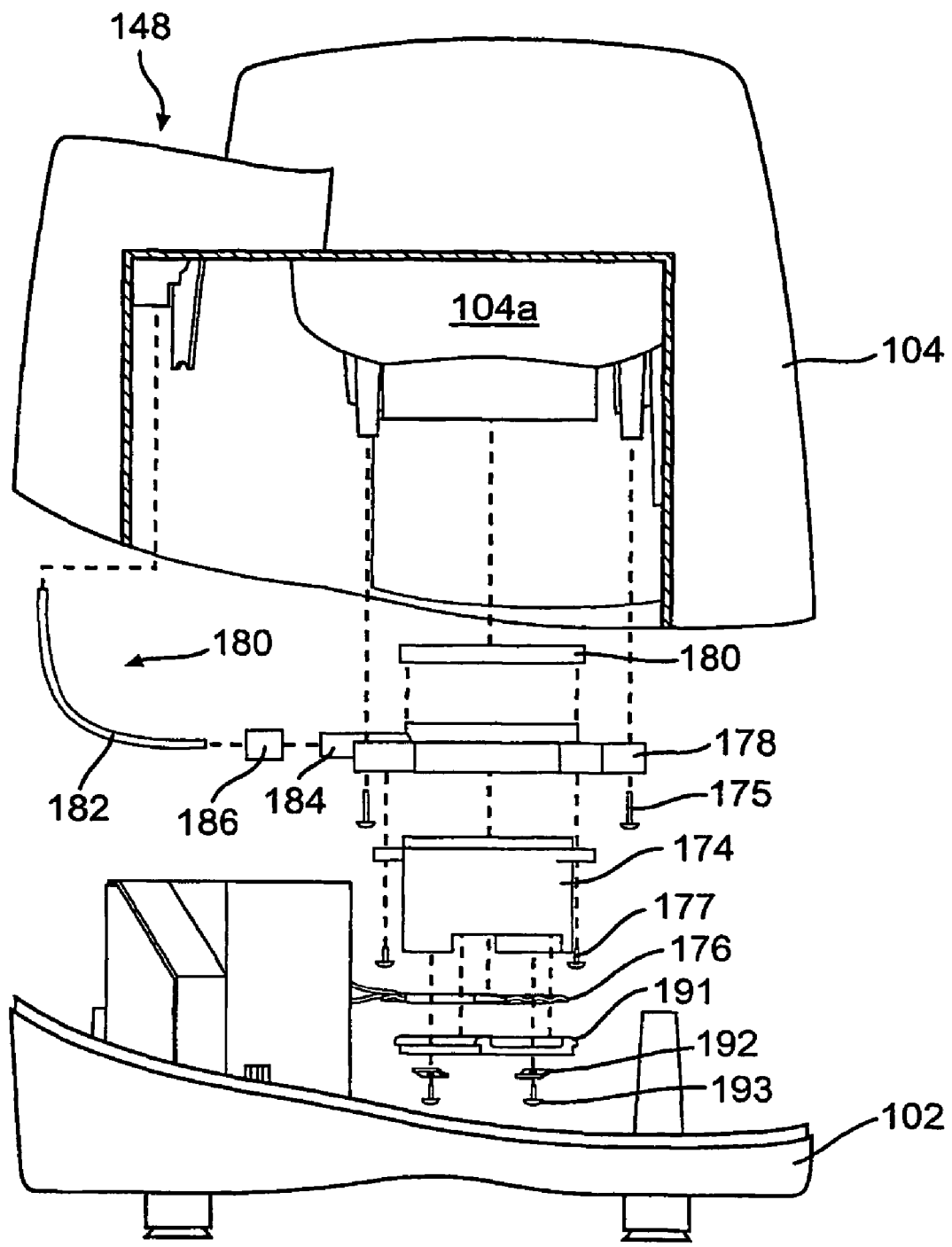
FIG. 7d is an exploded plan view of the base, body, and heating system according to a preferred embodiment of the invention.

As seen in FIG. 6, a heating system 172 is mounted to the bottom surface of the lower chamber 104a by means of a manifold 178.

The manifold 178 serves three functions. First, it is preferably formed of a thermally-nonconductive material and thereby acts as a thermal buffer insulating the heating element mounting posts 162 from the heat generated by a heating element 176 and conducted by heating reservoir 174. Second, the manifold 178 provides a secure mounting surface for the heating reservoir 174 to the bottom surface of lower chamber 104a. Third, the manifold 178 includes a supply inlet formed in a sidewall thereof for allowing fluid to enter the heating reservoir 174. The manifold 178 may be affixed to the heating-element mounting posts 162 (shown in FIG. 5) by fasteners.

A circular gasket 180, which has an annular groove formed in one surface therein, is fitted to the concentric, annular projections 141, 142 so that an inside surface of the gasket is coextensive with bottom opening 142 formed in lower chamber 104a. The gasket 180 seals the interface between the manifold 178 and the bottom surface 144 of the lower chamber 104a. The seal formed by the gasket 180 prevents moist heat from escaping around and outside the lower chamber 104a. The gasket 180 may be formed of any of a variety materials known in the art that are suitable for the aforesaid purposes.

Referring to FIGS. 7a through 7d, the heating reservoir 174 is mounted to the manifold 178, which is positioned and secured to the center of the lower chamber 104a so that the heating reservoir 174 is disposed under the lower chamber 104a proximate to the opening 142 formed in the bottom of the lower chamber 104a.

The heating reservoir 174 is generally a vertically-oriented, cup-like basin. A heating element 176 is disposed under heating reservoir 174. The heating element 176 may be secured to the heating reservoir 174 by a channel-shaped bracket 191, a pair of tabs 192, and fasteners 193 secured to threaded holes in bosses 173, which are formed on the underside surface of heating reservoir 174.

The heating reservoir 174 is dimensioned to receive a specified quantity of fluid, e.g., water. The heating reservoir 174 may be fabricated from any number of efficient heat conducting noncorrosive materials, such as aluminum, which is relatively inexpensive, lightweight, durable, and an efficient conductor of heat.

The heating element 176 may be a resistive heating element. According to a preferred embodiment of the invention, a positive temperature coefficient (PTC) thermistor is used as the heating element 176.

In one aspect, PTC thermistors are particularly advantageous for use in the present invention because of their ability to function as self-regulating heating elements that operate at a nearly constant temperature over a broad range of voltage and dissipation conditions. Because PTC thermistors are self-regulating, they do not require a thermostat. (Although, as will be discussed hereinbelow, other embodiments of the invention contemplate the use of either a manual switch or an actuator switch, such as a thermostat, to allow the user to customize the operation of the apparatus.)

PTC thermistors typically are manufactured from semi-conducting barium titanate including small amounts of dopants. One such PTC thermistor is part number PH0OA24014725 manufactured by Faraday Enterprise, Ltd. of Hong Kong. Such PTC thermistors have no moving parts, are inexpensive, and long-lived.

A fluid-supply system 180 provided in body 104 includes a fluid-supply reservoir 148 and a fluid supply conduit 182 connected between the fluid-supply reservoir 148 and a supply inlet 184 provided in an annular manifold 178. The fluid-supply conduit 182 may be secured to supply tube 184 by means of an adhesive, such as silicone adhesive. In addition, a collar 186 may be fitted over the junction of the fluid-supply conduit 182 and the supply inlet 184 to make the connection even more secure.

The fluid-supply conduit 182 may be a flexible tube extending from the opening 150 (see FIGS. 4 and 5) formed in the bottom of the fluid-supply reservoir 144 to a supply inlet 184 integrally formed in manifold 178. Alternatively, the conduit 182 may be a rigid tube configured to extend from the fluid-supply reservoir 144 to the supply inlet 184 formed in manifold 178. The fluid-supply conduit 182 may be made of either plastic or a noncorrosive metal depending on the amount of flexibility/rigidity desired. Preferably, the fluid-supply conduit 182 is secured and sealed at the fluid-supply reservoir 144 by means of an adhesive, such as RTV silicone glue. In addition, an integrally-formed collar 151 may be formed around the drain hole 150 to provide an additional surface area for the adhesive to secure the conduit 182 to the fluid-supply reservoir 144.

FIGS. 8a through 8g show an article-holding basket 164, which is adapted and configured to hold a pair of articles. The article-holding basket 164 is preferably a unitary-molded component, generally configured of an open-mesh material with numerous openings, in the manner of a sieve. These openings not only allow fluid to drain freely from the articles retained by the article-holding basket 164 but also allow air to circulate though the article-holding basket 164 and thus around the articles.

Figure 8A:
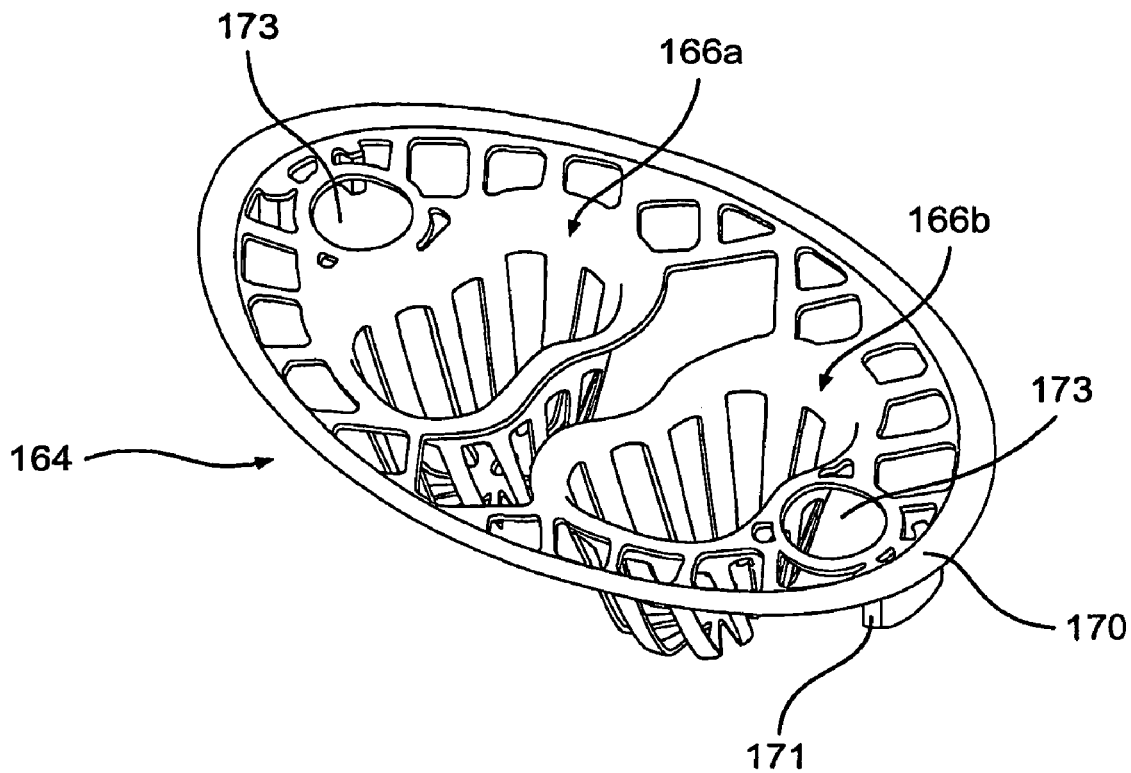
FIG. 8a is a perspective view of an article-holding basket according to a preferred embodiment of the invention.
Figure 8B:
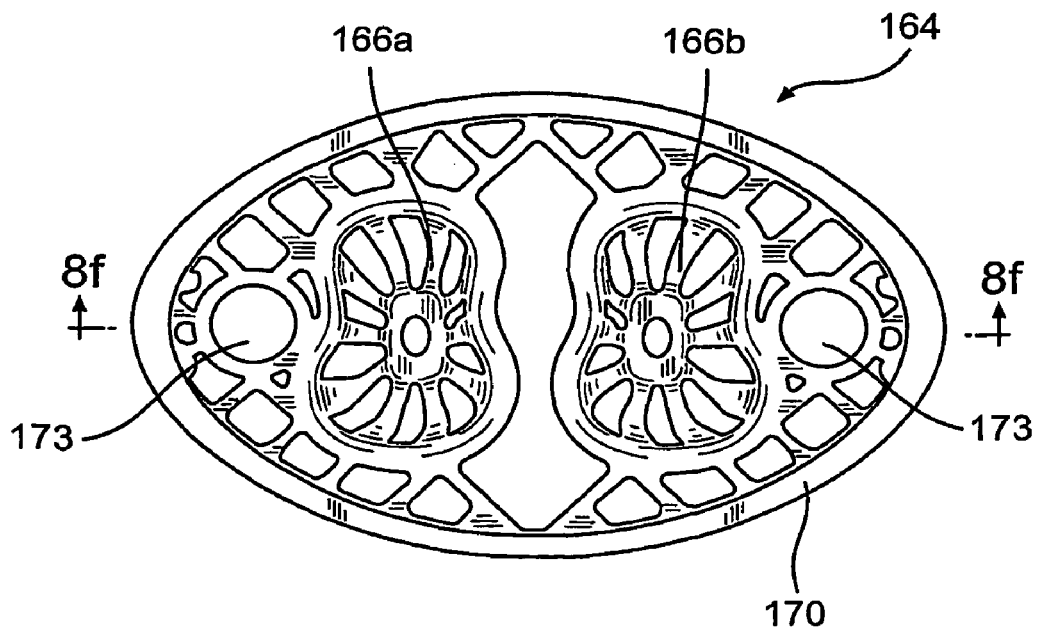
Figure 8C:
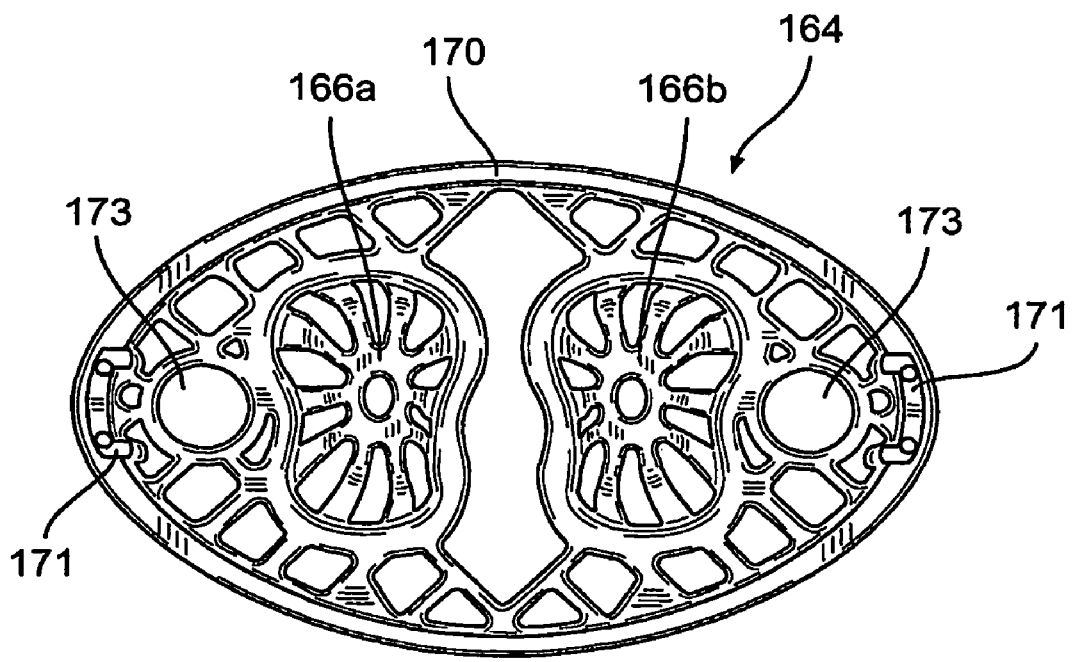
FIG. 8c is a bottom, plan view of the article-holding basket.
Figure 8D:
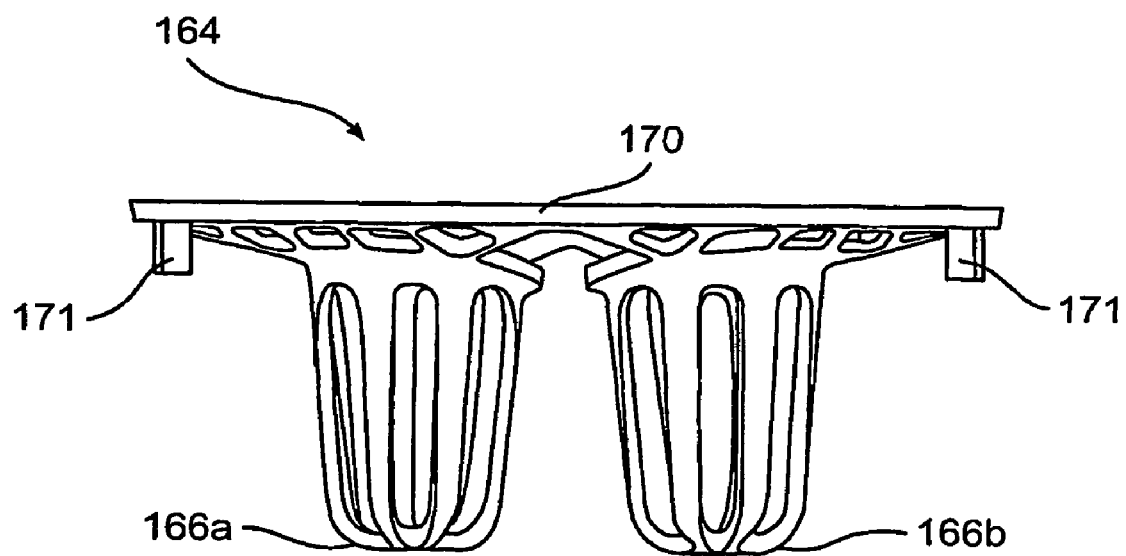
FIG. 8d is a front, elevational view of the article-holding basket.
Figure 8E:
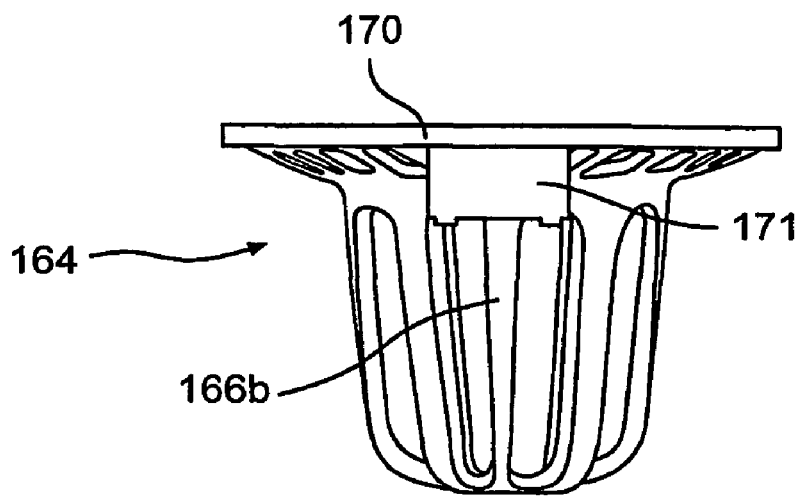
FIG. 8e is a side, elevational view of the article-holding basket.
Figure 8F:
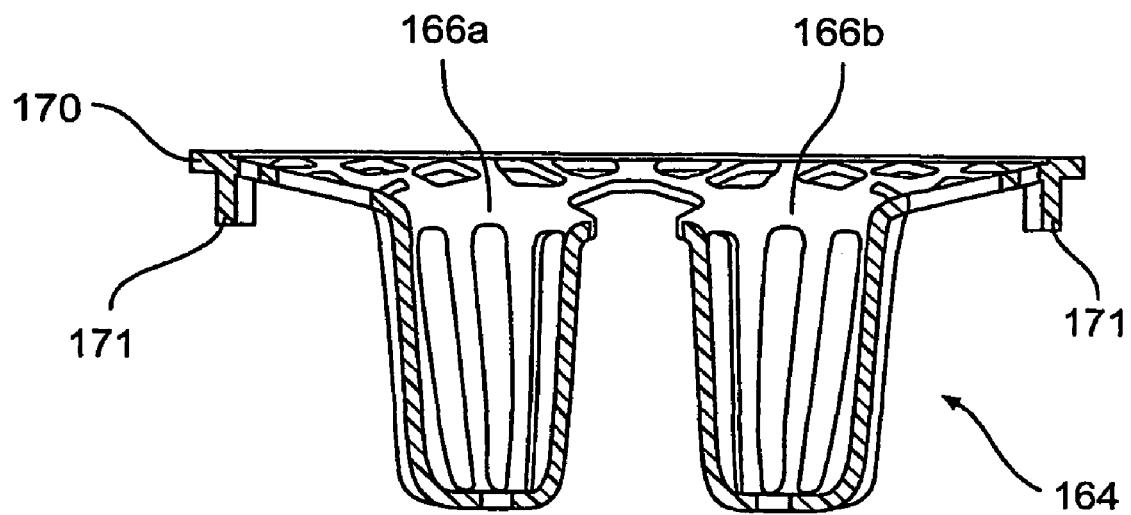
FIG. 8f is a cross-sectional view of the article-holding basket taken along lines 8f-8f in FIG. 8b.
Figure 8G:
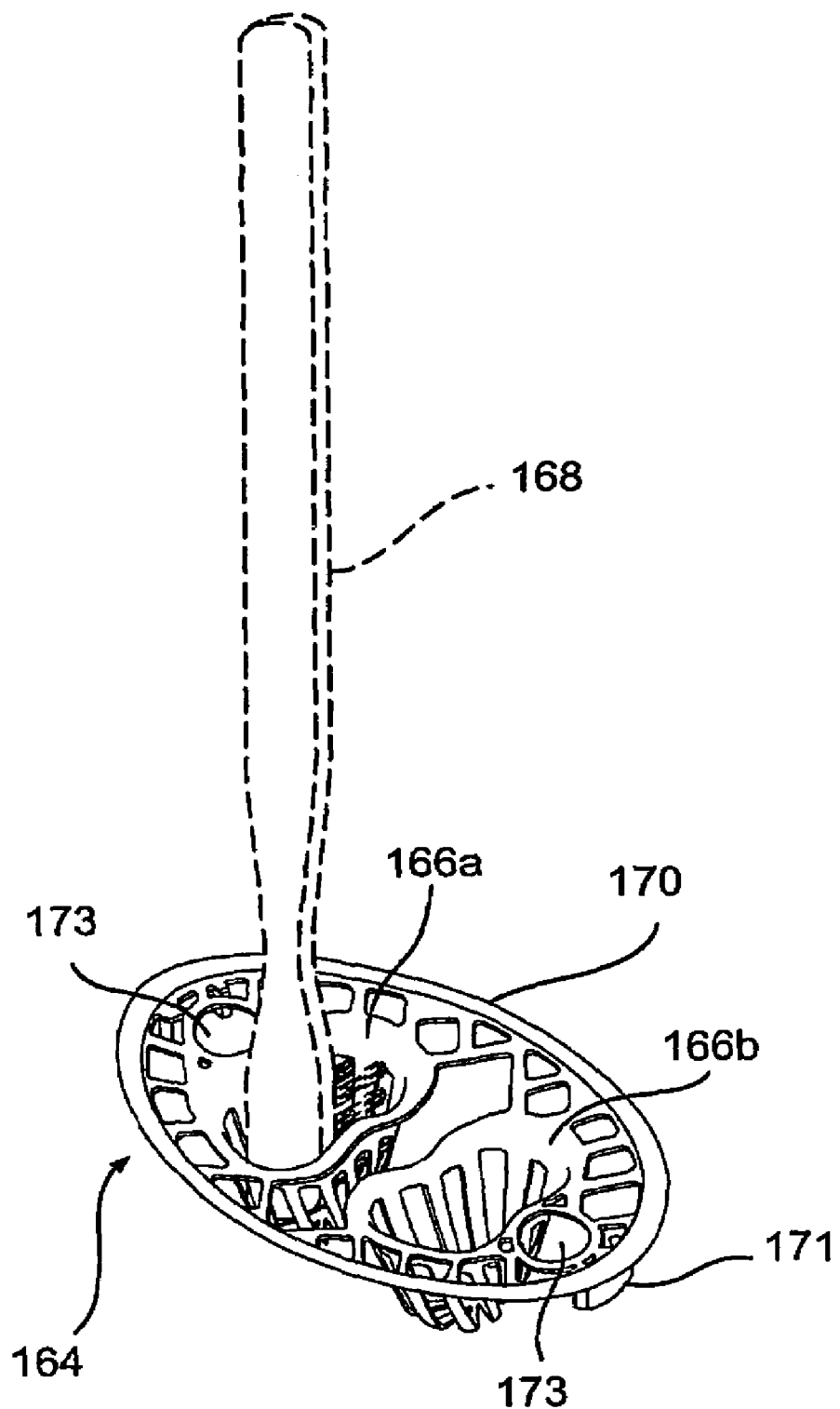
FIG. 8g is a perspective view of the article-holding basket shown in FIG. 8a with a conventional toothbrush secured therein.

In one embodiment, the article-holding basket 164 is elliptically-shaped and includes two compartments 166a, 166b. Each compartment is adapted and configured to receive and secure one end of the toothbrush 168 as shown in FIG. 8g. However, the exact configuration of the article-holding basket may be varied, depending on, inter alia, the type, shape, size, and number of articles to be held therein.

The article-holding basket 164 includes a peripheral flange 170, which cooperates with the shoulder 105 of the lower chamber 104a (shown in FIG. 4) to support the article-holding basket in a secure position when the article-holding basket 164 is seated in its nested position inside the lower chamber 104a.

A pair of tabs 171, which serve as positioning and securing members, are formed on opposing ends of a major axis of the elliptically-shaped article-holding basket 186. The pair of tabs cooperate with a pair of guide channels 145 formed on opposing sides of the lower chamber 104a, and guide the article-holding basket 164 into its nested position within the lower chamber 104a. The guide tabs 171 are dimensioned to provide an interference fit with the pair of guide channels 145. Such an arrangement ensures that the sterilized article 168 may be removed from the article-holding basket 164 without dislodging the article-holding basket 164 from the lower chamber 104a. Of course, additional guide tabs and guide channels may be provided to even better position and secure article-holding basket 164.

A pair of openings 173 formed on opposing ends of the article-holding basket 164 allow the upper ends of air delivery tubes 152a, 152b to pass through the article-holding basket 164.

The flange 170 and shoulder 105 may be mutually configured to provide a snap-fit. Such an arrangement further ensures that the toothbrush 168 may be removed from the article-holding basket 164 without dislodging the article-holding basket 164 from the lower chamber 104a. The article-holding basket 164 may be made from a noncorrosive material, such as aluminum, stainless steel, or a thermoplastic material.

Figures 9, 10:
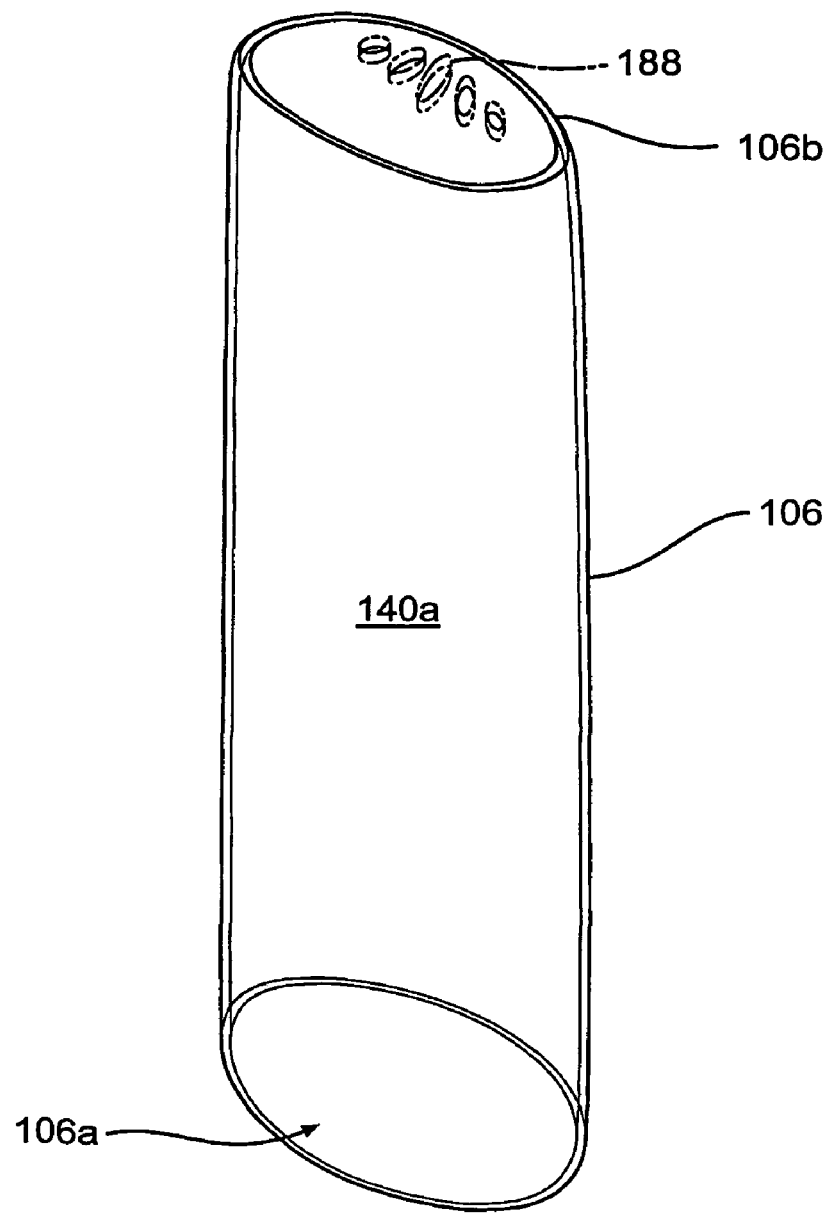
FIG. 9 is a perspective view of a removable measuring cup adapted and configured to be storable within a cavity formed in the body of the apparatus shown in FIGS. 1a, 1b, and 1c.
FIG. 10 is a perspective view of the cover of the apparatus shown in FIGS. 1a, 1b, and 1c.

FIG. 9 shows measuring cup 184 including a peripheral flange 186, which seats against the lip 146 (see FIG. 4) of the fluid-supply reservoir 144 when the measuring cup is received by the fluid-supply reservoir 144. The measuring cup 186 is conveniently stored in the fluid-supply reservoir 144 when it is not being used to fill the fluid-supply reservoir 144. Accordingly, the volume of the measuring cup 186 is less than that of each of the fluid-supply reservoir 144 and the heating reservoir 174 and is dimensioned to hold precisely the amount of fluid necessary to produce the amount of moist heat in the chamber to reduce a microbial population present on the surfaces of an article. Thus, the fluid-supply system 180 introduces a premeasured amount of a fluid, such as, for example, tap or distilled water, into the heating reservoir 174. Use of distilled water is preferable inasmuch as it will not result in sediment build-up in the fluid-supply system 180 and the heating system due to the mineral content of tap water. The measuring cup 184 contains approximately 5 to 9 cc of fluid. In a preferred embodiment, the measuring cup 184 contains approximately 7 cc of fluid. The shape of the fluid-supply reservoir 144 and the measuring cup 184 may vary from the configuration shown in the drawings depending on, inter alia, design and aesthetic considerations.

In FIG. 10, the cover 106 is shown to be a generally-elongated cylinder having an elliptical cross-section with an open bottom end 106a and a generally closed top end 106b. The inside space of cover 106 forms an upper chamber 140a. The open end 106a of the cover 106 shares the general same shape as the lower chamber 140b and is dimensioned to seat on top of the flange 170 of article-holding basket 164 when it is positioned in the lower chamber 140b with an interference fit. The result is a slight seal, which provides for a more effective operation, inasmuch as it prevents moist heat from escaping between the body 104 and the cover 106 prior to traveling the length of the retained article. Thus, when cover 106 is removably mounted to body 104, a chamber is formed which encloses the article. When seated on the body 102, the cover 106 is substantially vertically-oriented and surrounds and encloses the article, but does not contract the article.

One or more vent holes 166 are formed in the top end 106b of cover 106. The vent holes 188 are illustrated as being elliptically-shaped. The vents holes 188 allow air and cooler moist heat displaced by the hot moist heat produced during the moist-heat generating mode to escape from inside the cover 106 to the ambient environment. The vents 188 also allow the residual moist heat in the chamber 140 to escape during the dry-heat generating mode of the operating cycle to the ambient environment. Of course, the dimensions and shape of the cover 106 and vent holes 188 may vary depending on, inter alia, design and aesthetic considerations.

The body 102, base 104, cover 106, and measuring cup 184 are preferably made of a polymeric material that may be either thermally set or thermoplasticly formed. One particularly advantageous choice of material is a plastic treated with an antibacterial agent or an inorganic antimicrobial ceramic mix plastic. However, other suitable materials that provide adequate rigidity, durability, and dimensional stability are contemplated. Also, the base 102, body 104, cover 106, article-holding basket 164, and measuring cup 184 may be made in any suitable manner, such as by injection molding. These components may be opaque, transparent, or translucent. Further, the exterior surface of the apparatus 100 may bear aesthetic design details or otherwise may be configured, in part, to depict a fanciful character for novelty purposes, for example, to appeal to certain users of the apparatus, such as children.

FIG. 11 shows a power supply and current sensing circuit 1000, which is printed or otherwise formed on a circuit board and is secured between the side holders 116a, 116b formed in the base 102. The power supply and current sensing circuit 1000 includes the heating element 176, a 120 volt or 240 volt 50 or 60 Hz power source 1010, an operational amplifier 1030 to detect the moist-heat generating mode operation and the dry-heat mode operation, red and green LEDs 118a, 118b to indicate the moist-heat generating mode and the dry-heat generating mode, respectively. A PTC thermistor used as the heating element 176 provides a relatively low resistance below a predetermined switching temperature and a substantially higher resistance above the switching temperature. The heating element 176 exhibits a low resistance up to the water boiling temperature (212° F.) in the moist-heat generating mode to draw maximum electrical current and to provide maximum power for fast moist-heating. In the dry-heat generating mode after the water has evaporated, the heating element 176 is switched from a low resistance state to a high resistance state to draw minimal electrical current. The heat is regulated to insure that the maximum temperature of heating element 176 does not exceed approximately 400° F. Accordingly, the temperature range of the heating element 176 in the dry-heat generating mode is approximately 212° F. to 400° F. It should be understood that the present invention proceeds without the generation of significant amounts of steam. Technically, the only steam present in the apparatus is immediately above the top surface of the fluid in heating reservoir 174. Above that point, the steam quickly converts to moist heat upon rising.

The power supply and current sensing circuit 1000 senses the amount of current drawn by a heating element. When the amount of current drawn by the heating element exceeds the threshold value of the moist-heat generating mode, the LED 118a is illuminated. Conversely, when the amount of current drawn by the heating element is below the threshold value, the LED 118b is illuminated. In this way, the status indicator 118 communicates to a user the operational mode of the apparatus.

An AC voltage from the power source 1010 is supplied to the series connected heating element 176 and current limiting resistor 1042. An application manual switch S and/or actuator switch may be provided to interrupt the power supply. Rectifiers 1017 and 1018 rectify the power source AC voltage and a zener diode 1020 limits the DC voltage at the cathode of diode 1017 to a value appropriate for the operational amplifier 1030 and LEDs 118a, 118b. The current to zener diode 1020, the operational amplifier 1030 and LEDs 118a, 118b is supplied through a resistor 1014 in parallel with a capacitor 1015. A capacitor 1022 filters the rectified voltage across the zener diode 1020. The negative input to the operational amplifier 1030 is set at a threshold voltage value that distinguishes between the moist-heating generating mode operation and the dry-heat generating mode by a voltage divider formed by resistors 1024 and 1025. The voltage at the junction of the heating element 176 and the current limiting resistor 1042 is rectified by rectifier diodes 1044 and 1046. The DC voltage at the cathode of diode 1044 is filtered by a capacitor 1048 in parallel with a resistor 1049 and is applied to the positive input of the operational amplifier 1030.

During the moist-heat generating mode, the temperature of heating element 176 is below its switching temperature so that it is in its low resistance state and the DC voltage applied to the positive input of the operational amplifier 1030 is above the threshold voltage set at the negative input of the operational amplifier. A low voltage is obtained at the output of the operational amplifier 1030 and the red LED 118a, provided in base 102, is illuminated to indicate the moist-heat generating mode. During the dry-heat generating mode, the temperature of the heating element 176 switches from its low resistance state to its high resistance state to automatically keep the maximum temperature of the heating element 176 from exceeding 400° F. As a result of the resistance switching, the voltage at the junction of the resistance switching heating element 176 and the resistor 1042 is lower in the dry-heat operating mode than in the moist-heat generating mode. The lower voltage applied to the positive input of the operational amplifier 30 is less than the threshold voltage at its negative input. A high voltage is obtained at the output of operational amplifier 1030 and green LED 118b, provided in base 102, is illuminated to indicate the dry-heat generating mode.

The operation of the present invention, in one aspect, will now be discussed. For convenience, the operational cycle of one preferred embodiment of the present invention will be divided into and discussed in two separate modes, a moist-heat generating mode in which the apparatus subsequently delivers moist heat into the chamber, and a dry-heat generating mode in which the apparatus delivers dry heat into the chamber.

To initially energize the apparatus, the user simply plugs a power cord (not shown) of the apparatus into a conventional household electrical outlet, which immediately energizes the heating element 176 causing it to generate heat. Since no fluid is present in the heating reservoir 174, the heating element 176 draws a relatively low level of electrical current in comparison to its overall ability to draw current. The temperature of the heating element will rise to approximately 400° F. As a result, the heating element 176 only draws enough current sufficient to cause green LED 118b to be illuminated.

To reduce the microbial population present on the surfaces of an article such as, for example, a toothbrush for a dual-mode heating operation, the user removes the cover 106 from the body 104. The user inserts one end, preferably the brush end of the toothbrush into one of basket receptacles 166a, 166b of the article-holding basket 164. By continuing to press downward, the user presses the toothbrush into frictional engagement within the basket receptacle. When the brush head is so received, the toothbrush freely stands vertically and extends out of the chamber without contacting the sides of the chamber. Then, the user reinstalls the cover 106 over the chamber and toothbrush. The article-holding basket 164 is the only portion of the apparatus in contact with the toothbrush 168.

Initiating the moist-heat generating mode of a two-mode operational cycle will now be discussed. The user removes the measuring cup 184 from fluid-supply reservoir 148, fills the cup with fluid, and pours the fluid into the fluid supply reservoir 144. This automatically initializes the moist-heat mode of operation. Conveniently, the measuring cup 184 is dimensioned and/or marked to measure the desired amount of fluid. The fluid poured into the fluid supply reservoir 144 subsequently drains through a small hole in the bottom of the supply reservoir 148 through the fluid supply conduit 182 into the heating reservoir 174. Because of the small internal diameter of the fluid supply conduit 182 and its air-tight connection with fluid-supply reservoir 148 and the heating reservoir 174, a "capillary action" is created, which "draws" the fluid from supply reservoir 148 to the heating reservoir to effectively exhaust the liquid from the fluid supply reservoir thereby reducing the possibility of contamination of the fluid-supply reservoir with residual fluid.

The introduction of the fluid in the heating reservoir 174 causes the heating element 176 to cool down, thereby drawing an increased amount of current because of the inherent nature of the PTC thermistor heating element. When the current exceeds a known threshold, the current sensing circuit illuminates red LED 118*a*. As a result of the increased current drawn by the heating element 176, an increasing level of thermal energy is transferred to the fluid by the heating reservoir 174. When the temperature of the fluid reaches approximately 212° F., the fluid boils and generates local steam which is then converted into vapor as moist heat. It will be understood that the present invention does not rely on a significant amount of steam, but rather moist heat in the moist-heat generating mode to reduce a microbial population present on the surfaces of an article. The position of the heating reservoir 174 under the chamber 140 and at its lower open end serves to guide the moist heat into the chamber. The introduction of moist heat into the chamber 140 results in a convection current, causing an upward airflow from the heating reservoir 174, through the chamber 140 and the space enclosed by the cover 106, and finally through the cover via vents 188.

Moist heat that cools sufficiently by condensing on the inside wall of the cover 106 is converted back to a fluid state and flows down the inside of the cover 106 and the chamber 140, which chamber is shaped to direct the flow of the condensed fluid back into the heating reservoir 174. This "recycling" of moisture ensures that the toothbrush 168 in the chamber 140 is subjected to the moist heat for an increased period of time. Thus, the toothbrush 168 in the chamber is subjected to the warmest moist heat possible while the convection current also draws air from ambient environment into the chamber via the ambient air delivery tubes 152 to moderate the temperature in the chamber 140 thereby avoiding pressurized steam from being formed in the chamber 140.

Approximately 0.034 kw-min/cc is required to evaporate 1 cc of water. Accordingly, approximately 0.2366 kw-min, i.e., approximately 237 watt-min. of electricity is necessary to vaporize 7 cc of water. The PTC thermistor used as the heating element 174 described herein is specified at approximately 70 watts. However, measurements of the PTC thermistor 174 output vary between 65 and 70 watts. Nevertheless, a 70 watt heater will vaporize 7 cc's of water in approximately 4.83 minutes when 100% of the heat from the heater is conducted to the water.

The dry-heat generating mode of the two-mode operational cycle will now be discussed. When the quantity of fluid delivered to the heating reservoir, including the condensed fluid, is entirely exhausted, the dry-heat mode of operation is automatically initialized whereby the heating element 176 begins to draw less current. This dry-heat generating mode is sensed by the power supply and current sensing circuit 1000 which, when the amount of current drawn drops below a given threshold value, again illuminates the green LED 118*b*.

During the dry-heat generating mode, the convective air currents continue to draw ambient air into the chamber via the ambient air delivery tubes 152*a*, 152*b*. The ambient air, which is less moist than the residual air in the chamber, causes the evaporation and evacuation of moisture from the residual air within the chamber 140 out via the vents 188 in the cover 106. Thus, any article in the chamber 140, as well as the inside surface of the chamber and cover 106, will be caused to dry.

The aforesaid dry-heat generating mode continues until fluid is again introduced into the fluid-supply reservoir 144 by the user to begin another two-mode operational cycle. Accordingly, the processed article remains in a convenient, dry-storage environment without the user handling the article until the article is needed for its next use.

After all of the fluid in the heating reservoir 174 and the chamber 140 has been converted into moist heat and all of the moist heat has escaped from the apparatus, the PTC thermistor heating element 176 is no longer in an overcurrent state. Thus, the resistance of the PTC thermistor heating element 176 increases and the PTC heating element returns to its high temperature state, i.e., approximately 400° F. Accordingly, the apparatus is always energized and begin processing article(s) as long as it is connected to a source of power. Further, this "full time" energization yields convenience to a user of the apparatus since the user need only remove the cover, insert an article, reinstall the cover, and pour fluid into the supply reservoir to begin a moist-heat mode/dry-heat mode operation.

In certain instances, the user-may prefer to customize the operation of the apparatus by reducing the microbial population present on the surfaces of an article using only moist heat. Although such a single-mode operation may not be as efficacious as the dual mode operation described above, it still serves the purpose of reducing the microbial population present on the surfaces of the article. To effect this mode of operation, the user may simply remove the article from the apparatus after the moist-heat mode is concluded. Given that the article is in a chamber, which is not filled with pressurized steam, the user will not be subject to scalding when removing the article from the apparatus even though moist heat may be present. Alternatively, the user may simply unplug the apparatus power supply cord from the power outlet to deenergize heating element 176 at any time during or at the conclusion of the moist-heat generating mode.

In another embodiment of the invention, a manually-operated switch S and/or an actuator-operated switch A, such as a thermistor, may be provided to control the flow of electrical current to the power supply and current sensing circuit 1000. This allows the user to operate the present invention only in the moist-heat generating mode. The actuator may be either a thermal control, such as a thermostat, or a timer control either of which may be manually overridden by switch S, to disconnect the electrical current from flowing into the power supply and current supply circuit 1000 even before the thermal control or timer disconnects the heating element 174 from the source of power. Examples of such thermal controls include a disc thermostat-mounted reset sold by Selco, Orange, Calif.; thermal control from Portage Electric Products, Inc., North Canton, Ohio; or KLIXON® thermal products from Texas Instruments, Dallas. Of course, other such thermal controls would be known to one of ordinary skill.

In yet other instances, the user may prefer to customize the operation of the apparatus by reducing the microbial population present on the surfaces of an article using only dry heat. Although such a single-mode operation may not be as efficacious as the dual mode operation described above, it still serves the purpose of reducing the microbial population present on the surfaces of the article. To effect this mode of operation, the user may simply insert the article into the apparatus while it is in a dry-heat mode. Given that the article is in a chamber, which is not filled with pressurized steam, the user will not be subject to scalding when removing the article.

The following dry-heat generating mode measurements were observed with a Wavetek Tm45 digital thermometer with a stated accuracy of plus/minus 2 to 3° F.

The apparatus was turned on and allowed to temperature stabilize for several hours.

Each measurement was taken over a several minute time span to average the air flow fluctuations and to allow the temperature probe to stabilize. The article-holding basket was removed to facilitate the measuring process.

The temperature probe was inserted into the center hole of the five vent holes 188 formed at the top of the cover 106. The probe was then lowered in one inch increments, allowed to stabilize and the temperature ranges were observed at each step. Care was taken to keep the temperature probe in the middle of the space (front to back and side to side) at each step.

Below are the recorded temperature ranges starting at the top (0") and continuing in 1" increments down to the bottom of the basket level approximately at eight inches below the top.

| Level (inches) | Temperature (° F.) |
|---|---|
| 0 (top) | 117-119 |
| 1 | 123-127 |
| 2 | 128-133 |
| 3 | 131-138 |
| 4 | 136-144 |
| 5 | 142-152 |
| 6 | 147-159 |
| 7 | 154-170 |
| 8 | 179-200 |
| (basket bottom) | |

As a preliminary investigation to assess the efficacy of the apparatus 100 and four toothbrushes (Soft) were tested as below.

Morning aqueous brushings/solutions from five volunteers was collected and the toothbrushes were dipped into the solutions (bristles down) for five minutes under mild agitation with a stir-bar. Then the toothbrushes were treated as follows:

0 Control (Untreated).
1 30 min in the disclosed apparatus (Unit #1) with the brush in upright position.
2 4 hours in the disclosed apparatus (Unit #2) with the brush in upright position.
3 30 min in the disclosed apparatus (Unit #3) with the brush in downward (normal) position.

At the end of the treatment time, the toothbrushes were removed from the apparatuses and were assayed for general microbial populations using culture tests.

The control (untreated) brush showed abundant microbial colonies, while none of the three treatments showed any microbial colonies. These tests, while establishing the brushes to be adequately viable, prove that the disclosed apparatus is effective in reducing the microbial population on the toothbrushes.

It will be understood that while some elements described herein are said to be integrally formed with other elements, other fabrication techniques, such as press-fitting, heat and ultrasonic welding, adhesion, and the like may also be employed.

It will also be understood that while certain materials such as antimicrobial, thermoplastic may have been mentioned herein, other materials may be employed taking into consideration various design criteria, such as dimensions, weight, strength, size, and the like and aesthetic criteria.

While the present invention has been described with respect to what are currently considered to be the preferred embodiments, including components, materials, shapes, dimensions, and types of compounds it is to be understood that the claimed invention is not limited to the disclosed embodiments.

The scope of the following claims should be accorded the broadest interpretation so as to encompass all such modifications and equivalent structures and functions. Further, the invention is intended to cover various modifications and equivalent arrangements included within the spirit and scope of the accompanying claims.

What is claimed is:

1. An apparatus for reducing a microbial population present on the surfaces of an article, said apparatus comprising:
    a heating system for receiving a fluid, said heating system having a first mode for generating moist heat by converting the received fluid into the moist heat, and a second mode for generating dry heat automatically after generating the moist heat;
    a fluid-supply system for supplying the fluid to said heating system;
    a base,
    a body removably secured to and in contact with an uppermost surface of said base,
    a cover removably mounted on said body, wherein said heating system is disposed above said base, said cover including at least one vent, and
    a chamber defined by said body and said cover, for securing and enclosing the article therein and receiving the moist heat and the dry heat generated by said heating system,
    wherein said heating system operates at a first energy level in the first mode while generating the moist heat and at a second energy level in the second mode while generating the dry heat and
    wherein, during generation of the moist heat in the first mode, said at least one vent allows the moist heat to escape to the ambient environment,
    whereby the microbial population present on the surfaces of the article is reduced.

2. The apparatus of claim 1, wherein said heating system includes a manifold, a heating reservoir mounted to said manifold to receive the fluid from said fluid-supply system, and a heating element disposed proximate to said heating reservoir, thereby heating the fluid received in said heating reservoir.

3. The apparatus of claim 2, wherein said heating element is one of an electric resistance-type heating element, a ceramic-type heating element, a coil-type heating element, and a positive temperature coefficient element.

4. The apparatus of claim 3, wherein said heating element comprises a positive temperature coefficient thermistor.

5. The apparatus of claim 4, wherein a temperature generated by said positive temperature coefficient thermistor is in the range of approximately 212° F. to 400° F.

6. The apparatus of claim 4, wherein a temperature within said chamber is in the range of approximately 117° F. to 200° F.

7. The apparatus of claim 2 further comprising a heat reflector disposed on an inside surface of said base below said heating element to reflect radiant heat from said heating element toward said heating reservoir.

8. The apparatus of claim 7, wherein said heat reflector comprises a reflective material adhered to a top surface of said base.

9. The apparatus of claim 8, wherein said reflective material is aluminum foil.

10. The apparatus of claim 2 further comprising at least one heat reflector disposed on an inside surface of said body proximate to said heating element to reflect radiated heat from said heating element toward said heating reservoir.

11. The apparatus of claim 10, wherein said heat reflector comprises a reflective material adhered to an inside surface of said body.

12. The apparatus of claim 11, wherein said reflective material is aluminum foil.

13. The apparatus of claim 11, further comprising a measuring cup adapted and configured to hold a predetermined quantity of fluid, wherein said fluid-supply reservoir is dimensioned to removably receive said measuring cup in a nesting manner for storage of said measuring cup.

14. The apparatus of claim 13, wherein said measuring cup includes a peripheral flange formed proximate to an opening of said measuring cup, wherein said flange is supported on a perimeter of said fluid supply reservoir when said measuring cup is received by said fluid-supply reservoir for storage.

15. The apparatus of claim 1 further comprising an article-holding basket removably mounted in said chamber, said basket being adapted and configured to receive and retain the article.

16. The apparatus of claim 15, wherein said article-holding basket has an open-mesh configuration.

17. The apparatus of claim 15, wherein said article-holding basket is adapted and configured to snap-fit into said chamber.

18. The apparatus of claim 15, wherein said article-holding basket comprises at least one compartment adapted and configured to receive at least a portion of the article therein and to retain the article vertically so that the article is otherwise not in contact with said apparatus.

19. The apparatus of claim 1, further comprising a temperature moderating system to moderate the temperature in said chamber by allowing ambient air to enter said chamber.

20. The apparatus of claim 19, wherein said temperature moderating system comprises at least one air supply tube being adapted and configured to allow ambient air to enter said chamber from air that is present in a space below said chamber.

21. The apparatus of claim 1, wherein at least one opening is provided in a top surface of said cover to allow air to escape from said chamber.

22. The apparatus of claim 1, wherein said cover is made of an opaque material.

23. The apparatus of claim 1, wherein said cover is made of a transparent material.

24. The apparatus of claim 1, wherein said cover is made of a translucent material.

25. The apparatus of claim 1, wherein the generation of the dry heat automatically follows the generation of the moist heat.

26. The apparatus of claim 1, wherein each of the moist-heat generating mode and the dry-heat generating mode produces a convective airflow in said chamber.

27. The apparatus of claim 1, further comprising a first circuit board holder for holding a circuit board in a horizontal direction, said circuit board holder being integrally formed with said base.

28. The apparatus of claim 27, wherein said first circuit board holder includes a pair of channel-shaped side holders each adapted and configured to receive an edge of a circuit board, wherein said circuit board is engaged at opposing edges by said pair of channel-shaped holders.

29. The apparatus of claim 27, further comprising a second circuit board holder for holding said circuit board in a vertical direction, said second circuit board holder being integrally formed with said body.

30. The apparatus of claim 27, wherein a power supply and current sensing circuit is formed on said circuit board.

31. The apparatus of claim 30 further comprising a status indicator provided in said base and responsive to said power supply and current sensing circuit, said status indicator indicating whether said heating system is operating in a moist-heat generating mode or a dry-heat generating mode.

32. The apparatus of claim 31, wherein said status indicator comprises a pair of LEDs.

33. The apparatus of claim 32, wherein said pair of LEDs includes a first LED provided to indicate the moist-heat generating mode and a second LED provided to indicate the dry-heat generating mode.

34. The apparatus of claim 30, wherein said power supply and current sensing circuit includes a switch for disconnecting a supply of power to said heating system.

35. The apparatus of claim 34, wherein said switch is manually operated.

36. The apparatus of claim 34, wherein said switch is actuator operated.

37. The apparatus of claim 36, wherein said switch is a thermostat.

38. The apparatus of claim 36, wherein said switch is a timer.

39. An apparatus for reducing a microbial population on the surfaces of an article, said apparatus comprising:
   a heating system for receiving a fluid, converting the received fluid into moist heat in a first mode, and generating dry heat in a second mode automatically after generating the moist heat;
   a fluid-supply system for supplying the fluid to said heating system; wherein said fluid supply system comprises a fluid supply reservoir to receive fluid, and a fluid supply conduit to deliver fluid from said fluid supply reservoir to said heating system:
   a removable cover including at least one vent;
   a body for receiving said cover, wherein said cover is vertically elongated so as to define a chamber substantially above an uppermost surface of said body, said chamber enclosing the article and receiving the moist heat and the dry heat from said heating system;
   a base to support said body; and
   a measuring cup adapted and configured to hold a predetermined quantity of fluid, wherein said fluid-supply reservoir is dimensioned to removably receive said measuring cup in a nesting manner for storage of said measuring cup,
   wherein said heating system operates at a first energy level in the first mode, while generating the moist heat and at a second energy level in the second mode, while generating the dry heat, and
   wherein, during generation of the moist heat in the first mode, said at least one vent allows the moist heat to escape to the ambient environment,
   whereby the microbial population present on the surfaces of the article is reduced.

40. The apparatus of claim 39, wherein said measuring cup includes a peripheral flange formed proximate to an opening of said measuring cup, wherein said flange is supported on a perimeter of said fluid supply reservoir when said measuring cup is received by said fluid-supply reservoir for storage.

41. An apparatus for reducing a microbial population on the surfaces of an article, said apparatus comprising:
- a heating system for receiving a fluid, converting the received fluid into moist heat in a first mode, and generating dry heat in a second mode automatically after generating the moist heat;
- a fluid-supply system for supplying the fluid to said heating system;
- a removable cover including at least one vent;
- a body for receiving said cover, wherein said cover is vertically elongated so as to define a chamber substantially above an uppermost surface of said body, said chamber enclosing the article and receiving the moist heat and the dry heat from said heating system;
- a base to support said body; and
- a first circuit board holder for holding a circuit board in a horizontal direction, said first circuit board holder being integrally formed with said base,
- wherein said heating system operates at a first energy level in the first mode, while generating the moist heat and at a second energy level in the second mode, while generating the dry heat,
- wherein, during generation of the moist heat in the first mode, said at least one vent allows the moist heat to escape to the ambient environment, and
- wherein said first circuit board holder includes a pair of channel-shaped side holders each adapted and configured to receive an edge of a circuit board, and wherein said circuit board is engaged at opposing edges by said pair of channel-shaped holders,
- whereby the microbial population present on the surfaces of the article is reduced.

42. An apparatus for reducing a microbial population on the surfaces of an article, said apparatus comprising:
- a heating system for receiving a fluid, converting the received fluid into moist heat in a first mode, and generating dry heat in a second mode automatically after generating the moist heat;
- a fluid-supply system for supplying the fluid to said heating system;
- a removable cover including at least one vent;
- a body for receiving said cover, wherein said cover is vertically elongated so as to define a chamber substantially above an uppermost surface of said body, said chamber enclosing the article and receiving the moist heat and the dry heat from said heating system;
- a base to support said body;
- a first circuit board holder for holding a circuit board in a horizontal direction, said first circuit board holder being integrally formed with said base; and
- a second circuit board holder for engaging a top edge of said circuit board in a vertical direction, said second circuit board holder being integrally formed with said body.
- wherein said heating system operates at a first energy level in the first mode, while generating the moist heat and at a second energy level in the second mode, while generating the dry heat, and
- wherein, during generation of the moist heat in the first mode, said at least one vent allows the moist heat to escape to the ambient environment, 43. An apparatus for reducing a microbial population on the surfaces of an article, said apparatus comprising:
- a heating system for receiving a fluid, converting the received fluid into moist heat in a first mode, and generating dry heat in a second mode automatically after generating the moist heat;
- a fluid-supply system for supplying the fluid to said heating system;
- a removable cover including at least one vent;
- a body for receiving said cover, wherein said cover is vertically elongated so as to define a chamber substantially above an uppermost surface of said body, said chamber enclosing the article and receiving the moist heat and the dry heat from said heating system;
- a base to support said body, and
- an article-holding basket removably mounted in said chamber, said basket being adapted and configured to receive and retain the article,
- wherein said heating system operates at a first energy level in the first mode, while generating the moist heat and at a second energy level in the second mode, while generating the dry heat,
- wherein, during generation of the moist heat in the first mode, said at least one vent allows the moist heat to escape to the ambient environment,
- wherein said fluid supply system comprises a fluid supply reservoir to receive fluid, and a fluid supply conduit to deliver fluid from said fluid supply reservoir to said heating system,
- wherein said fluid-supply reservoir includes a drain hole and a first end of said fluid-supply conduit is in fluid communication with said drain hole,
- wherein a collar is integrally formed with said fluid-supply reservoir around said drain hole to receive said first end of said fluid-supply conduit,
- wherein said first end of said fluid-supply conduit is secured to said collar by means of an adhesive,
- wherein a second end of said fluid-supply conduit is in fluid communication with said manifold,
- wherein said fluid-supply system includes a collar around said second end of said fluid-supply conduit and said manifold, and
- wherein said article-holding basket is adapted and configured to snap-fit into said chamber,
- whereby the microbial population present on the surfaces of the article is reduced.

* * * * *